(12) United States Patent
Stetefeld

(10) Patent No.: US 9,880,141 B2
(45) Date of Patent: Jan. 30, 2018

(54) DETECTION AND RECOVERY OF CHEMICAL ELEMENTS FROM FLUIDS WITH TECTRABRACHION

(71) Applicant: University of Manitoba, Winnipeg (CA)

(72) Inventor: Joerg Stetefeld, Winnipeg (CA)

(73) Assignee: University of Manitoba, Winnipeg, Manitoba (CA)

( * ) Notice: Subject to any disclaimer, the term of this patent is extended or adjusted under 35 U.S.C. 154(b) by 0 days.

(21) Appl. No.: 14/399,892

(22) PCT Filed: May 6, 2013

(86) PCT No.: PCT/CA2013/000450
§ 371 (c)(1),
(2) Date: Nov. 7, 2014

(87) PCT Pub. No.: WO2013/166585
PCT Pub. Date: Nov. 14, 2013

(65) Prior Publication Data
US 2016/0153952 A1    Jun. 2, 2016

(51) Int. Cl.
| | |
|---|---|
| *C07K 14/195* | (2006.01) |
| *G01N 33/18* | (2006.01) |
| *G01N 33/68* | (2006.01) |
| *G01N 33/84* | (2006.01) |
| *C02F 101/10* | (2006.01) |
| *C02F 101/20* | (2006.01) |

(52) U.S. Cl.
CPC ....... *G01N 33/1813* (2013.01); *C07K 14/195* (2013.01); *G01N 33/182* (2013.01); *G01N 33/1866* (2013.01); *G01N 33/68* (2013.01); *G01N 33/84* (2013.01); *C02F 2101/101* (2013.01); *C02F 2101/20* (2013.01); *C02F 2305/00* (2013.01)

(58) Field of Classification Search
CPC .............. C07K 2319/73; C07K 14/245; C07K 14/435; C07K 16/1232; C07K 16/18; C07K 2317/76; C07K 2319/21; C07K 2319/55; A61K 2039/542; A61K 2039/55505; A61K 2039/55544; A61K 2039/55566; A61K 2039/6031; A61K 2039/6037; A61K 39/015; A61K 39/385; A61K 39/39; A61K 47/48261; A61K 47/4833; A61K 2039/53; A61K 2039/552; A61K 39/0005; A61K 39/0258
See application file for complete search history.

(56) References Cited

U.S. PATENT DOCUMENTS 8,580,274 B2 *   11/2013   Arakawa .............. A61K 39/015
                                                           424/134.1

FOREIGN PATENT DOCUMENTS

WO    WO20100092963 A1 *  8/2010

* cited by examiner

*Primary Examiner* — Padmavathi Baskar
(74) *Attorney, Agent, or Firm* — Gowling WLG (Canada) LLP

(57) ABSTRACT

The present disclosure provides uses and methods for using compositions comprising a tetrabrachion protein from *Staphylothermus marinus* or a fragment thereof for detecting and/or recovering a chemical element from a solution or a suspension. The fragment of the tetrabrachion protein includes the right handed coiled coil (RHCC).

3 Claims, 12 Drawing Sheets

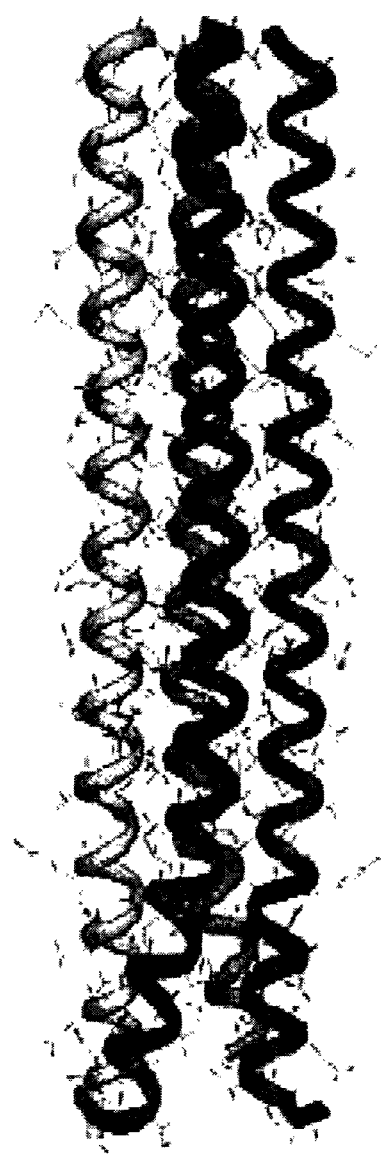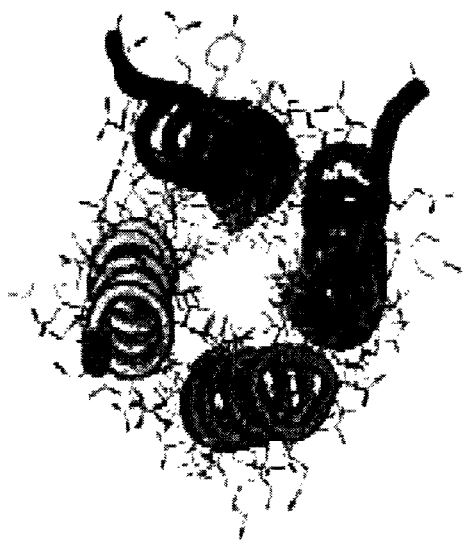
Fig. 3

```
   1 mnrvlaysll aimtlsllii papgiaqrit vgvsvkagty nfynitpttq tvevtdngml
  61 rviinrteat elgttirlaf ildtdkydpn vggyflnvsn igvyapsdpt qspyggvidi
 121 tqnstltdgt qvvgnvtvvn ggnnviilid lsklpdlqnv vyitnvytet sttanltntl
 181 lrvkafdaas wdavisgnqf kilyipslck yvkinvihsp aivgtnvdvi vsfhkyfslv
 241 qsiagvsldi tvdnktqlnm tnyynateny vlatfingnl tvggsevfss ptvtvinast
 301 fkysgqvkdy aptvadtatp wvrtlnkfev efrheivnxt hdlifyihcd sdtvsydtwp
 361 flivnasldi tttevafnst tinpgdivnf tahnvplqyl tatnygvlrf qlinpalvvy
 421 vpvsnmtlsa ntttgiings fvlpdapygg ldyltylvfn dgkfiangyi tvspcietyv
 481 ltntsayaed agssyigrfv pgytsvpgdy ivikgygfal snltgftvsi nntdviilna
 541 tynastgkii ilaklldtng tpipvgagfi rvgqngttni ayapfnvtrn sglekvlfnp
 601 rwfyngtyyi ehdklgdpyl yfpvdyplvn ntfttemwpf nttievigwp tntftlkafn
 661 kefnlsfnll tlsltngynm tnlynltipf lpygnytlle gtllsvnnrt vftvhmginv
 721 dldscgngtl sitvvgaapn teynftfgyq vhdlnygitr yispqwngtw nislvtdiyg
 781 tgstsvplit lyptsyvina twdvitwlrl sgsgtldllf svdvsyngft dnlttpityv
 841 fgpsdttpgs fniyvnttyn vsvvrvavdy lprtnvvisv petvlpgdti tvqifphhne
 901 vwgfieptal fdenqllgwy ltvrlvdpls ntvvervagy yagnlivedv dgdgdnevwf
 961 vvnltaplvl gvdktyrvdv elflavlnps snitgvtavd necyvqldln gtiywnglgs
1021 gimlggdgqi vtvlgvlegk ldtikdgiae inatvndint ylkvnvtdll ktinnsvvmi
1081 kndtatliig qaeikakldd llnltsqvnd tvtmilaccn naskvlnrme gtlnstytgv
1141 lnvksdlstl idtannvvip kfnelydnvt veinasrdli iqkissvnds lttiisagfn
1201 dveamisnln ttllnridel egtllfymta neqrlegiin etaddivyrl tviiddryes
1261 lknlitlrad rlemiindnv stilasignv nltvfnklnd leielgdvna tinagifqiq
1321 snlgnanqli ldtltsskve ilnaissnas aisseihnav nqlstlvlqv ndtltlkitg
1381 eadnilnfls slegsmntgf nnvtstlsav ennilgkitd tsnllsskid ntlstlqdli
1441 tstsndlkns issakndivs slsskvdsst qtlstklddl ksaqesntns innnimlfga
1501 aslillivti glvgyrliar rrvg
```

```
SEQ ID NO:2   1    M   G   S   S   H   H   H   H   H   H   S   S   G   L   V   P   R   G   S   I
SEQ ID NO:3   5317 ATG GGC AGC AGC CAT CAT CAT CAT CAC CAC AGC AGC GGC CTG GTT CCG CGT GGA TCC ATC

21   I   N   E   T   A   D   D   I   V   Y   R   L   T   V   I   D   D   R   Y
              5377 ATC AAC GAA ACC GCT GAC GAC ATC GTT TAC CGT CTG ACC GTT ATC GAC GAC CGT TAC

41   E   S   L   K   N   L   I   T   L   R   A   D   R   L   E   M   I   N   D
              5437 GAA TCT CTG AAA AAC CTG ATC ACC CTG CGT GCT GAC CGT CTG GAA ATG ATC AAC GAC

61   N   V   S   T   I   L   A   S   I   *   *
              5497 AAC GTT TCT ACC ATC CTG GCT TCT ATC TAA TAA
```

⬆
                          Thrombin cleavage site

Fig. 8

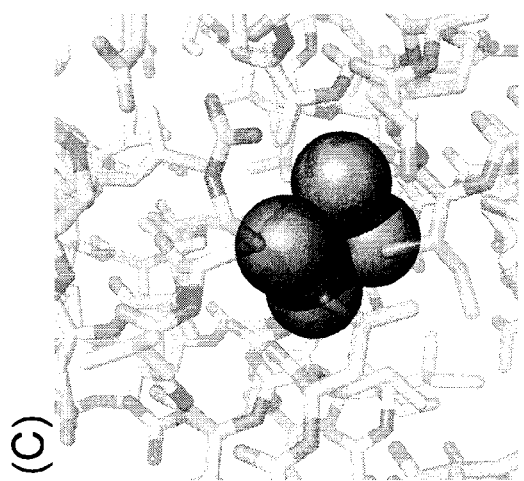
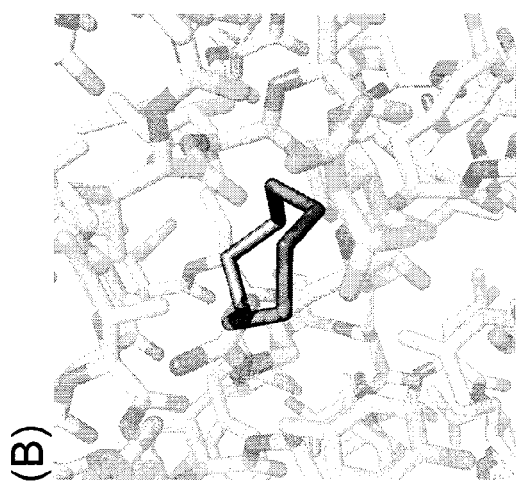
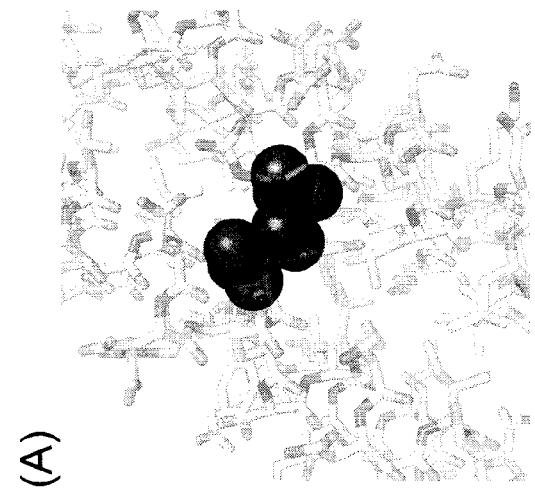
Fig. 9

(A) Water cluster
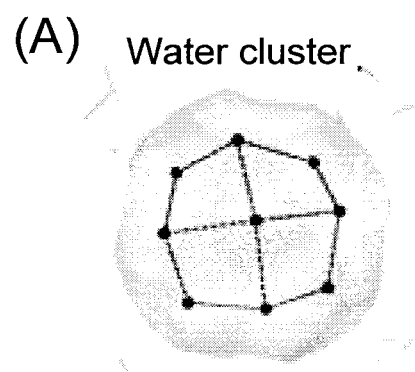
$\Delta G = -34$ kJ/mol
(B) S8 cluster
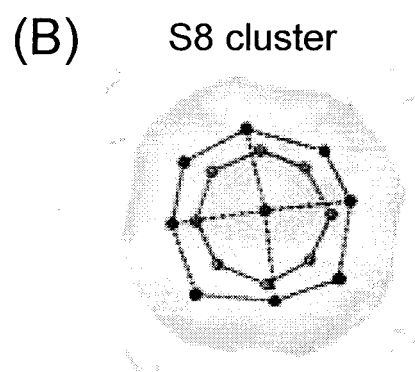
$\Delta G = -84$ kJ/mol
(C) S10 cluster
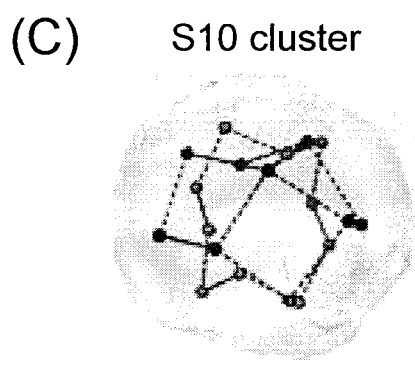
$\Delta G = -58$ kJ/mol
Fig. 10

DETECTION AND RECOVERY OF CHEMICAL ELEMENTS FROM FLUIDS WITH TECTRABRACHION

SEQUENCE LISTING

This application contains a Sequence Listing electronically submitted via EFS-WEB to the United States Patent and Trademark Office as an ASCII text file entitled "RHCC polypeptide chain_ST25.txt" created on 2012-05-07. The information contained in the Sequence Listing is incorporated by reference herein.

FIELD OF THE INVENTION

The present disclosure relates to methods and compositions for detection and/or recovery of chemical elements from solutions and/or suspensions. More specifically, the present disclosure pertains to compositions comprising a tetrabrachion protein from *Staphylothermus marinus* and/or fragments thereof, and to uses of the compositions for detecting and/or recovering chemical elements from solutions and/or suspensions.

BACKGROUND OF THE INVENTION

Many types of organic liquids, such as various forms of petroleum, oil, "sour" gas, fuel, organic solvents and other hydrocarbons, as well as waste water, mine tailings, oils, coal and effluents of various processes contain sulfur (S). The presence of sulfur in these liquids has been correlated with damage to both the natural environment as well as to man-made environments. For example, sulfur in petroleum has led to the corrosion of pipelines, pumping and refinery equipment, and premature breakdown of combustion engines. In addition, combustion of sulfur-containing liquids results in sulfur dioxide pollution of the atmosphere, thereby contributing significantly to extended occurrences in acid rain. Acid rain has lasting deleterious effects on aquatic and forest ecosystems, as well as agricultural areas located downwind of combustion facilities. To combat these problems, several methods for desulfurizing fuels and coal have been developed.

When sulfur is predominantly present in its organic forms, it can be removed chemically by hydro-desulfurization processes, which involve reacting natural gas, hydrocarbon-based fuels and other such products with hydrogen gas at elevated temperatures in the presence of selected catalysts. These methods have many technical shortcomings and are quite expensive. As a result, many practitioners of this art have turned their attention to microbial desulfurization processes (MDS) as potentially viable alternative options; that is, the use of microbial metabolic processes to desulfurize liquids.

Several microorganisms have metabolic pathways involving sulfur. The metabolic pathways of bacteria such as those exemplified by *Thiobacillus* sp., *Sulfolobus* sp., *Hansenula* sp., and *Cryptococcus albidus*, have been used for removing sulfur from coal and/or coal slurries. *Rhodococcus* sp. and their enzyme derivatives, in combination with hydro-desulfurization methods, have also been used to remove organic sulfur from hydrocarbon fuels. Other microorganisms exemplified by *Rhodococcus rhodochrous, Bacillus sphaericus, Pseudomonas* sp., *Campylobacter* sp., *Leptospirillum ferrooxidans, Thiobacillus ferrooxidans* and a variety of mixed cultures have also been used for removing sulfur from various liquids.

Sulfur and sulfur-containing compounds removed from organic liquids, waste water, mine tailings, oils, coal and effluents of various processes can be used in numerous industrial applications. For example, sulfur and/or sulfur-containing compounds can be used to manufacture cellophane and rayon, can be used as a component of fertilizers, can be used in pharmaceuticals, dyestuffs and agrochemicals, can be used as a fungicide or pesticide and can be used in fermenting wine.

SUMMARY OF THE INVENTION

The present disclosure provides a use of tetrabrachion protein or a fragment thereof from *Staphylothermus marinus* or a composition comprising tetrabrachion protein or a fragment thereof for detecting and/or recovering chemical elements from solutions and/or suspensions. The present disclosure further discloses methods for detecting and/or recovering chemical elements from solutions and/or suspensions using a tetrabrachion protein or a fragment thereof.

According to an aspect of the present disclosure, use of a tetrabrachion protein or a fragment thereof from *S. marinus* for detecting and/or recovering chemical elements from solutions and/or suspensions is disclosed.

According to another aspect of the present disclosure, a use of a composition comprising a tetrabrachion protein or a fragment thereof from *S. marinus* and a carrier therefor for detecting and/or recovering chemical elements from solutions and/or suspensions is disclosed.

According to a further aspect of the present disclosure, a method for detecting and/or recovering chemical elements from solutions and/or suspensions is disclosed, wherein the method comprises: (a) introducing *S. marinus* into the solution to produce tetrabrachion protein or a fragment thereof; and (b) providing conditions that permit the tetrabrachion protein or the fragment thereof to recover a chemical element from a solution and/or a suspension.

According to another aspect of the present disclosure, a method for detecting and/or recovering a chemical element from a solution and/or a suspension is disclosed, wherein the method comprises: (a) introducing tetrabrachion protein or a fragment thereof from *S. marinus* into the solution; and (b) providing conditions that permit the tetrabrachion protein or the fragment thereof to recover the chemical element from a solution and/or a suspension.

According to another aspect of the present disclosure, a method for detecting and/or recovering a chemical element from a solution and/or a suspension is disclosed, wherein the method comprises: (a) a composition comprising tetrabrachion protein or a fragment thereof from *S. marinus* into the solution; and (b) providing conditions that permit the tetrabrachion protein or the fragment thereof to recover the chemical element from a solution and/or a suspension.

A further aspect of the present disclosure is a method for detecting and/or recovering a chemical element from a solution and/or a suspension, wherein the method comprises: (a) introducing a nucleic acid construct encoding tetrabrachion protein or a fragment thereof into a host cell; (b) incubating the host cell under conditions that permit expression of the nucleic acid construct, thereby producing tetrabrachion protein or the fragment thereof; (c) introducing the host cell into the solution; and (d) providing conditions that permit the tetrabrachion protein or fragment thereof to recover a chemical element from a solution and/or a suspension.

BRIEF DESCRIPTION OF THE DRAWINGS

The features of the present disclosure will become more apparent from the following description in which reference is made to the appended drawings wherein:

FIG. 3 shows the RHCC domain of tetrabrachion. FIG. 5(a) shows a side view of the four helices of the RHCC domain of tetrabrachion at 1.8 Å resolution. The N-terminus is at the bottom, and the C-terminus is at the top of the figure. FIG. 5(b) shows an axial view from the N-terminus of the RHCC domain;

FIG. 4 shows an amino acid sequence of a tetrabrachion protein from *S. marinus* (SEQ ID NO: 1);

FIG. 5 shows a 52-amino-acid sequence of the RHCC polypeptide chain fragment of tetrabrachion (SEQ ID NO: 2);

FIG. 8 shows a listing of the amino acid sequence (SEQ ID NO: 2) of a RHCC polypeptide chain fragment of tetrabrachion and the codon-optimized nucleotide sequence (SEQ ID NO: 3) encoding the RHCC polypeptide chain fragment used in the exemplary embodiments of the present disclosure;

FIG. 9(A) shows an exemplary crystal structure of a portion of the RHCC polypeptide chain fragment of tetrabrachion with a symmetric cluster of nine water molecules, while FIG. 9(B shows an exemplary crystal structure of a portion of the RHCC polypeptide chain fragment of tetrabrachion with a highly ordered $S_8$ sulfur cluster;

FIG. 10 shows the largest hydrophobic cavity of the RHCC polypeptide chain fragment of tetrabrachion bound to a cluster of nine water molecules, bound to an $S_8$ sulfur cluster and bound to an $S_{10}$ sulfur cluster, with their respective free energy values.

DETAILED DESCRIPTION

Figure 1:
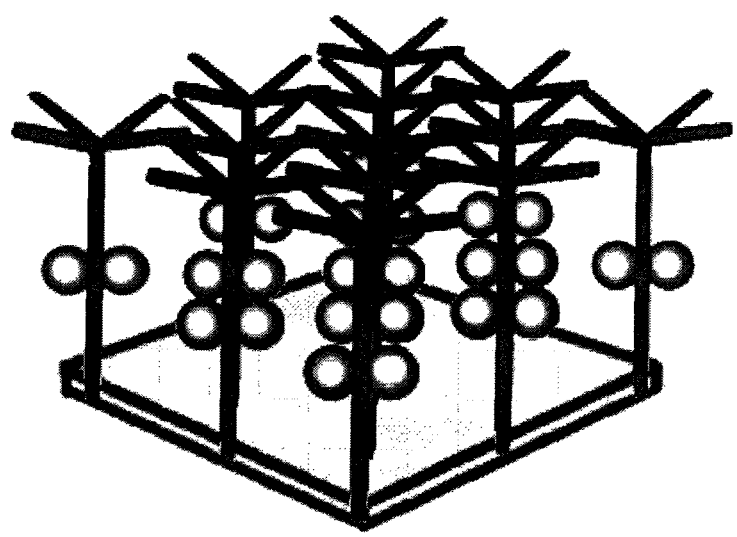
FIG. 1 shows an exemplary diagrammatic representation of the canopy-like arrangement of the tetrabrachion stalk anchored to the *Staphylothermus marinus* cell membrane.

The present disclosure pertains to compositions, to methods for the use of the compositions, and to use of the compositions for detection and/or recovery of chemical elements from solutions and/or suspensions.

Unless defined otherwise, all technical and scientific terms used herein have the same meaning as commonly understood by one of ordinary skill in the art to which the invention belongs. Certain terms are discussed in the specification to provide additional guidance to the practitioner in describing the methods, uses and the like of embodiments of the invention, and how to make or use them. It will be appreciated that the same thing may be said in more than one way. Consequently, alternative language and synonyms may be used for any one or more of the terms discussed herein. No significance is to be placed upon whether or not a term is elaborated or discussed herein. Recital of one or a few synonyms or equivalents does not exclude use of other synonyms or equivalents, unless it is explicitly stated. Use of examples in the specification, including examples of terms, is for illustrative purposes only and does not limit the scope and meaning of the embodiments of the invention herein. Although any methods and materials similar or equivalent to those described herein can be used in the practice or testing of the present invention, the preferred methods and materials are now described.

To facilitate understanding of the disclosure, the following definitions are provided.

As used herein, "recover", "recovered", "recovering" or "recovery" refers to the obtaining of and/or extraction of and/or separation of one or more chemical elements from a solution and/or a suspension.

As used herein, "solution" refers to any chemical element-containing liquid including, without limitation, any organic liquid, waste water, mine tailings, oils, coal and effluents produced by various processes.

As used herein, "suspension" refers to any suspension or slurry that is a heterogeneous mixture containing solid particles of chemical elements.

As used herein, "sulfur" refers to any sulfur-containing compound, elemental sulfur ($S_0$) and any other sulfur allotrope, such as, without limitation, $S_8$ and $S_{10}$.

As used herein, "STABLE" refers to the stalk-associated archaeabacteria endo-protease proteins that bind specifically to the right-handed coiled coil polypeptide chain fragment of the tetrabrachion protein from *Staphylothermus marinus*

As used herein, "RHCC" refers to the right-handed coiled coil polypeptide chain fragment of tetrabrachion from *S. marinus* comprising 52 amino acid residues and to which the STABLE protease binds.

As used herein, "host cell" refers to a cell of any microorganism into which a nucleic acid construct encoding tetrabrachion or a fragment thereof can be transformed. The host cell is not to be considered limiting in any manner, and can be, but is not limited to, a mammalian cell, an insect cell, a bacterial cell or a yeast cell, exemplified by and including, without limitation, *Escherichia* sp., *Pseudomonas* sp., *Bacillus* sp., *Saccharomyces* sp., *Schizosaccharomyces* sp. and *Candida* sp.

As used herein, the term "synthetic DNA" means DNA sequences that have been prepared entirely or at least partially by chemical means. Synthetic DNA sequences may be used, for example, for modifying native DNA sequences in terms of codon usage and expression efficiency.

The word "comprise" or variations such as "comprises" or "comprising" will be understood to imply the inclusion of a stated integer or groups of integers but not the exclusion of any other integer or group of integers.

As used herein, the word "complexed" means attached together by one or more linkages.

The term "a cell" includes a single cell as well as a plurality or population of cells.

The term "about" or "approximately" means within 20%, preferably within 10%, and more preferably within 5% of a given value or range.

The term "nucleic acid" refers to a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes cDNA, genomic DNA, synthetic DNA, and semisynthetic DNA.

The term "gene" refers to an assembly of nucleotides that encode a polypeptide, and includes cDNA and genomic DNA nucleic acids.

The term "recombinant DNA molecule" refers to a DNA molecule that has undergone a molecular biological manipulation.

The term "vector" refers to any means for the transfer of a nucleic acid into a host cell. A vector may be a replicon to which another DNA segment may be attached so as to bring about the replication of the attached segment. A "replicon" is any genetic element (e.g., plasmid, phage, cosmid, chromosome, virus) that functions as an autonomous unit of DNA replication in vivo, i.e., capable of replication under its own control. The term "vector" includes plasmids, DNA-protein complexes, and biopolymers. In addition to a nucleic acid, a vector may also contain one or more regulatory regions, and/or selectable markers useful in selecting, measuring, and monitoring nucleic acid transfer results (transfer to which tissues, duration of expression, etc.).

The term "cloning vector" refers to a replicon, such as plasmid, phage or cosmid, to which another DNA segment may be attached so as to bring about the replication of the attached segment. Cloning vectors may be capable of replication in one cell type, and expression in another ("shuttle vector").

A cell has been "transfected" by exogenous or heterologous DNA when such DNA has been introduced inside the cell. A cell has been "transformed" by exogenous or heterologous DNA when the transfected DNA effects a phenotypic change. The transforming DNA can be integrated (covalently linked) into chromosomal DNA making up the genome of the cell.

The term "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms.

Modification of a genetic and/or chemical nature is understood to mean any mutation, substitution, deletion, addition and/or modification of one or more residues. Such derivatives may be generated for various purposes, such as in particular that of enhancing its production levels, that of increasing and/or modifying its activity, or that of conferring new pharmacokinetic and/or biological properties on it. Among the derivatives resulting from an addition, there may be mentioned, for example, the chimeric nucleic acid sequences comprising an additional heterologous part linked to one end, for example of the hybrid construct type consisting of a cDNA with which one or more introns would be associated.

Likewise, for the purposes of the invention, the claimed nucleic acids may comprise promoter, activating or regulatory sequences, and the like.

The term "promoter sequence" refers to a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background.

The term "homologous" in all its grammatical forms and spelling variations refers to the relationship between proteins that possess a "common evolutionary origin," including homologous proteins from different species. Such proteins (and their encoding genes) have sequence homology, as reflected by their high degree of sequence similarity. This homology is greater than about 75%, greater than about 80%, greater than about 85%. In some cases the homology will be greater than about 90% to 95% or 98%.

"Amino acid sequence homology" is understood to include both amino acid sequence identity and similarity. Homologous sequences share identical and/or similar amino acid residues, where similar residues are conservative substitutions for, or "allowed point mutations" of, corresponding amino acid residues in an aligned reference sequence. Thus, a candidate polypeptide sequence that shares 70% amino acid homology with a reference sequence is one in which any 70% of the aligned residues are either identical to, or are conservative substitutions of, the corresponding residues in a reference sequence.

The term "polypeptide" refers to a polymeric compound comprised of covalently linked amino acid residues. Amino acids are classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group. A polypeptide of the invention preferably comprises at least about 14 amino acids.

The term "protein" refers to a polypeptide which plays a structural or functional role in a living cell.

A coding sequence is "under the control" of transcriptional and translational control sequences in a cell when RNA polymerase transcribes the coding sequence into mRNA, which is then trans-RNA spliced (if the coding sequence contains introns) and translated into the protein encoded by the coding sequence.

The terms "codon optimization" and "codon optimized" mean the selection of appropriate DNA nucleotides for the synthesis of oligonucleotides of a sequence encoding a tetrabrachion protein or a fragment thereof using codons that are typically utilized within the target host.

The term "corresponding to" is used herein to refer to similar or homologous sequences, whether the exact position is identical or different from the molecule to which the similarity or homology is measured. A nucleic acid or amino acid sequence alignment may include spaces. Thus, the term "corresponding to" refers to the sequence similarity, and not the numbering of the amino acid residues or nucleotide bases.

The term "derivative" refers to a product comprising, for example, modifications at the level of the primary structure, such as deletions of one or more residues, substitutions of one or more residues, and/or modifications at the level of one or more residues. The number of residues affected by the modifications may be, for example, from 1, 2 or 3 to 10, 20, or 30 residues. The term derivative also comprises the molecules comprising additional internal or terminal parts, of a peptide nature or otherwise. They may be in particular active parts, markers, amino acids, such as methionine at position −1. The term derivative also comprises the molecules comprising modifications at the level of the tertiary structure (N-terminal end, and the like). The term derivative also comprises sequences homologous to the sequence considered, derived from other cellular sources, and in particular from cells of human origin, or from other organisms, and possessing activity of the same type or of substantially similar type. Such homologous sequences may be obtained by hybridization experiments. The hybridizations may be performed based on nucleic acid libraries, using, as probe, the native sequence or a fragment thereof, under conventional stringency conditions or preferably under high stringency conditions.

The term "operatively linked" means that the particular sequences, for example a regulatory element and a coding region of interest, interact either directly or indirectly to carry out an intended function, such as mediation or modulation of gene expression. The interaction of operatively linked sequences may, for example, be mediated by proteins that interact with the operatively linked sequences. A coding region of interest, such as the nucleotide sequence encoding tetrabrachion protein, may also be introduced within a vector along with other sequences, typically heterologous, to produce a chimeric construct. A transcriptional regulatory region and a sequence of interest are "operably linked" when the sequences are functionally connected so as to permit transcription of the sequence of interest to be mediated or modulated by the transcriptional regulatory region.

The terms "regulatory region" and "regulatory element" mean a nucleic acid sequence that has the property of controlling the expression of a sequence that is operatively linked with the regulatory region. Such regulatory regions may include promoter or enhancer regions, and other regulatory elements recognized by one of skill in the art. By "promoter" it is meant the nucleotide sequences at the 5' end of a coding region, or fragment thereof, that contain all the signals essential for the initiation of transcription and for the regulation of the rate of transcription. There are several types of regulatory elements, including those that are inducible, constitutive or the like. A regulatory element may be derived from any suitable source provided that the regulatory element is active in the host cell. A regulatory element may be an animal nucleic acid sequence, a bacterial nucleic acid sequence, a viral nucleic acid sequence, a protozoan nucleic acid sequence, or a yeast nucleic acid sequence, provided that the regulatory element functions within the host cell in which it is used. A regulatory element may comprise, in whole or in part, synthetic nucleic acid sequences not found in nature (a synthetic regulatory element).

*Staphylothermus marinus* is a marine hyperthermophilic Archaea microorganism, isolated from geothermally heated sediments and from a "black smoker" on the ocean floor. *S. marinus* requires elemental sulfur for growth. The optimum temperature for growth of *S. marinus* is 85° C. in minimal medium and 92° C. in rich medium. *S. marinus* is capable of tolerating wide ranges of pH (2-10), high redox potential, pressure and salinity. *S. marinus* possesses a filiform glycoprotein complex tetrabrachion that forms the surface (S-) layer of the organism (FIG. 1). The S-layer forms an assembly of protein molecules that coat the outside of the cell, thus providing the cell membrane of *S. marinus* protection against potentially damaging solutes and macromolecules.

Figure 2:
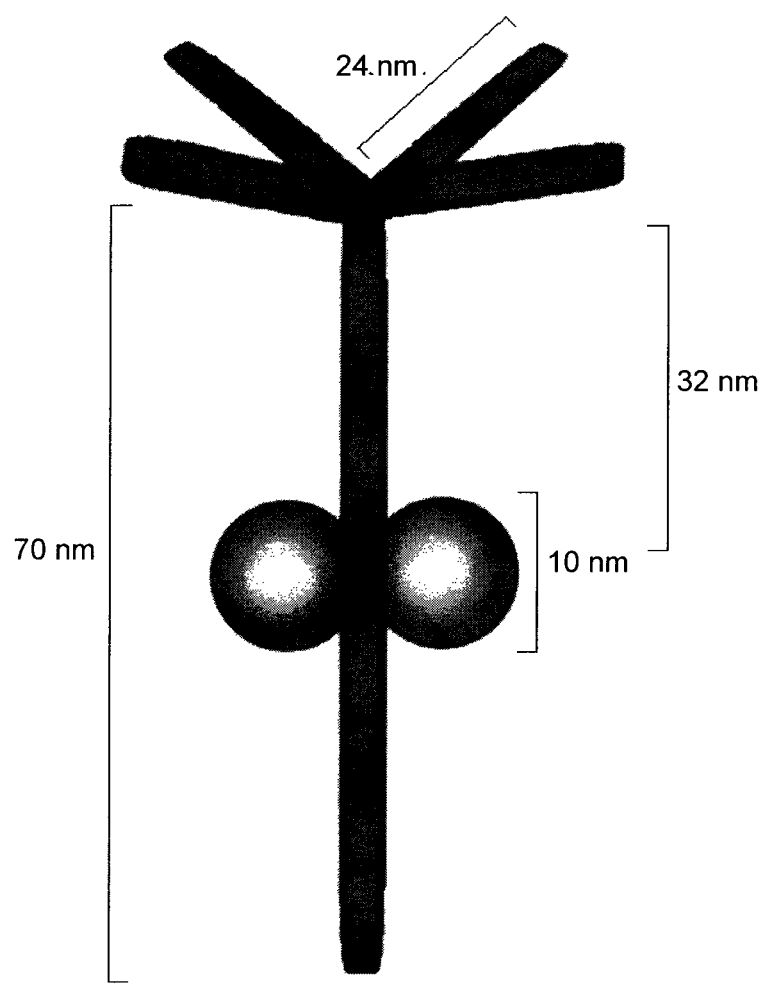
FIG. 2 shows an exemplary diagrammatic representation of the tetrabrachion stalk illustrating the dimensions of the tetrabrachion stalk. The spherical balls represent the STABLE protease that binds to the RHCC polypeptide chain fragment of tetrabrachion.

Tetrabrachion protein comprises an α-helical stalk of 70 nm in length that is anchored to the cell membrane at its C-terminal end, and an N-terminal domain consisting of four arms each approximately 24 nm in length formed of β-strands. The arms of the N-terminal domain form end to end contacts with the canopy-like meshwork of the *S. marinus* S-layer and give rise to a "quasi-periplasmic space" (FIG. 2).

The α-helical stalk of tetrabrachion comprises four copies of a "heavy" chain polypeptide that together form a parallel four-stranded α-helical coiled coil that is membrane-anchored (FIG. 3(a)). At the top of the coiled coil portion, there is a hinge domain at which point the four heavy chains diverge from each other and the four N-terminal arms are formed of "light" chain polypeptides (FIG. 3(b)).

The S-layer stalk of tetrabrachion is not uniform throughout its length. For example, the first 130 amino acid residues after the hinge show a classical heptad repeat motif that is characteristic of "left handed coiled coils". However, after Pro1160, the heptad repeat is replaced by an undecad repeat (an 11 amino acid residue repeat) that results in the formation of a right handed coiled coil (RHCC) structure or domain. A protease known as STABLE (stalk-associated archaeabacteria endo-protease) binds to the RHCC domain of tetrabrachion. A major feature of the tetrabrachion stalk domain is its extreme thermostability even in the presence of 1% (w/v) sodium dodecyl sulfate (SDS), 6M guanidine, or 70% (w/v) sulfuric acid.

Figure 5:
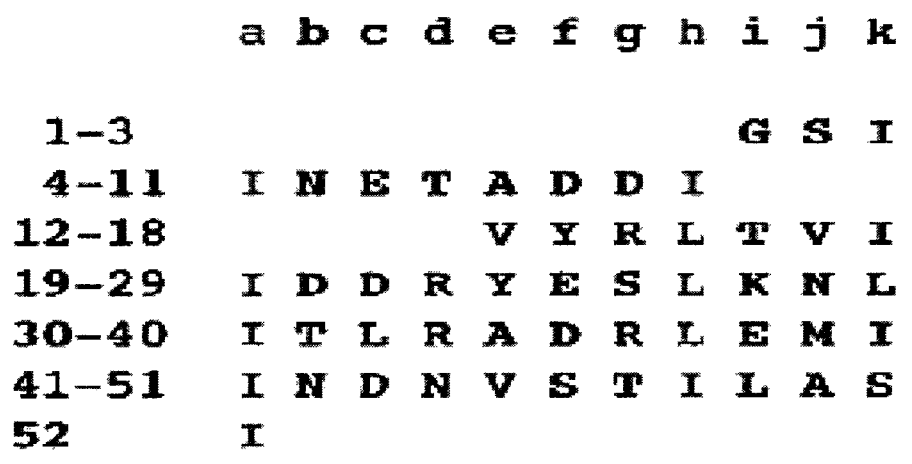

The RHCC structure of the stalk is a 52-amino-acid residue tetrameric bundled protein. (FIG. 4). The RHCC polypeptide chain fragment forms a parallel right-handed coiled coil with an average length of about 72 Å and width of about 25 Å. It has a 11/3 residue repeat, with the N-terminal part more supercoiled than the C-terminal part due to the presence of a stutter between Ile11 and Thr16 (FIG. 5). There is also a unique 7,4 residue repeat.

Figure 6:
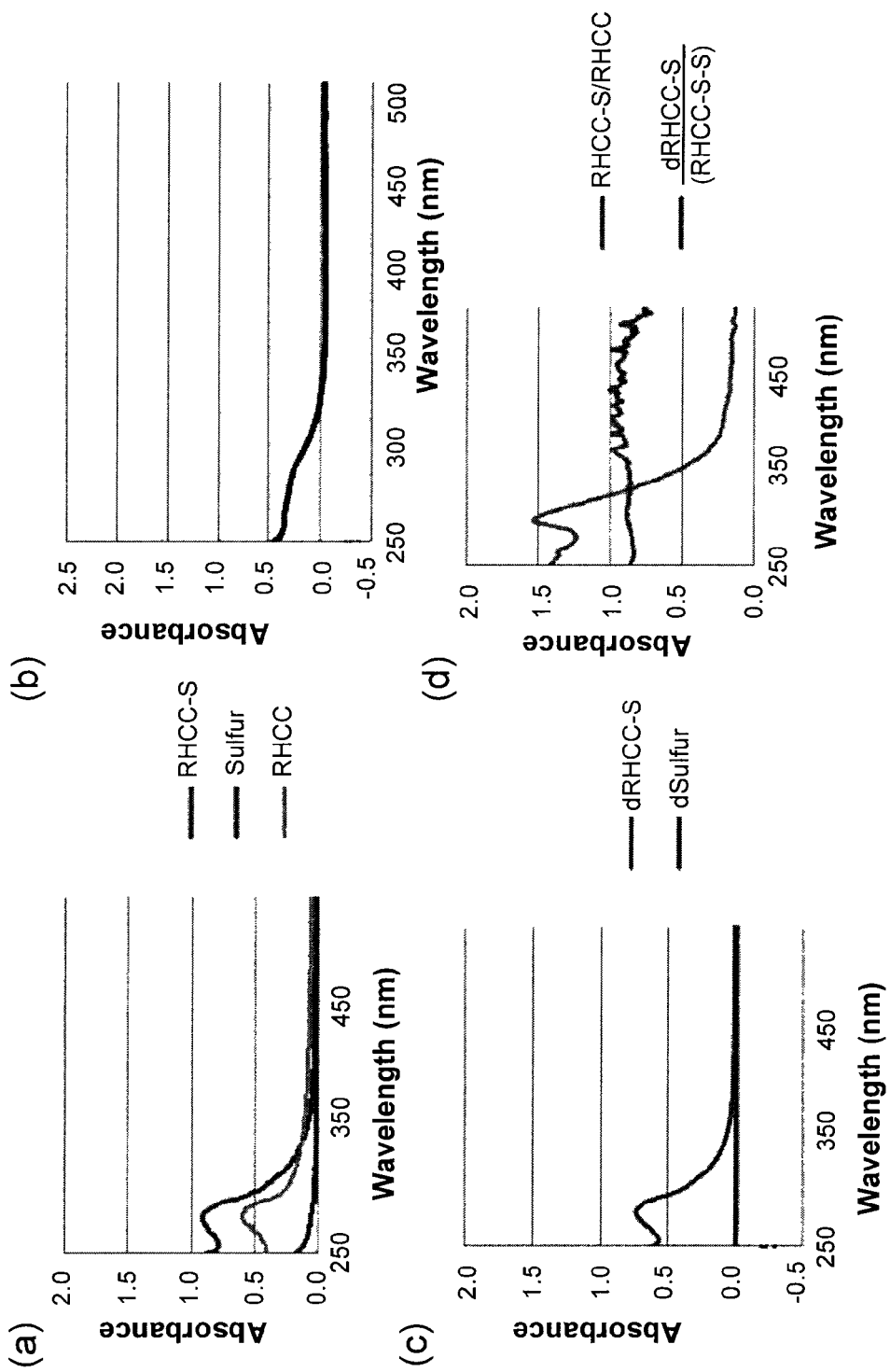
FIGS. 6(a)-6(d) are charts showing the absorption spectra of RHCC-sulfur incubation assays in Bicine. 6(a) shows the absorbance of the RHCC control, the sulphur control, and of RHCC incubated in the presence of sulphur, 6(b) shows the difference spectrum of RHCC and sulphur absorbance subtracted from the RHCC-sulfur absorbance, 6(c) shows the absorbance of the PHCC-sulfur and the sulphur control after dialysis, and 6(d) shows the absorbance ratio of the dialyzed RHCC-sulfur against un-dialyzed RHCC-sulfur (corrected for free sulphur in the solution) and the ratio of the absorbance of RHCC-sulfur to RHCC alone.
Figure 7:
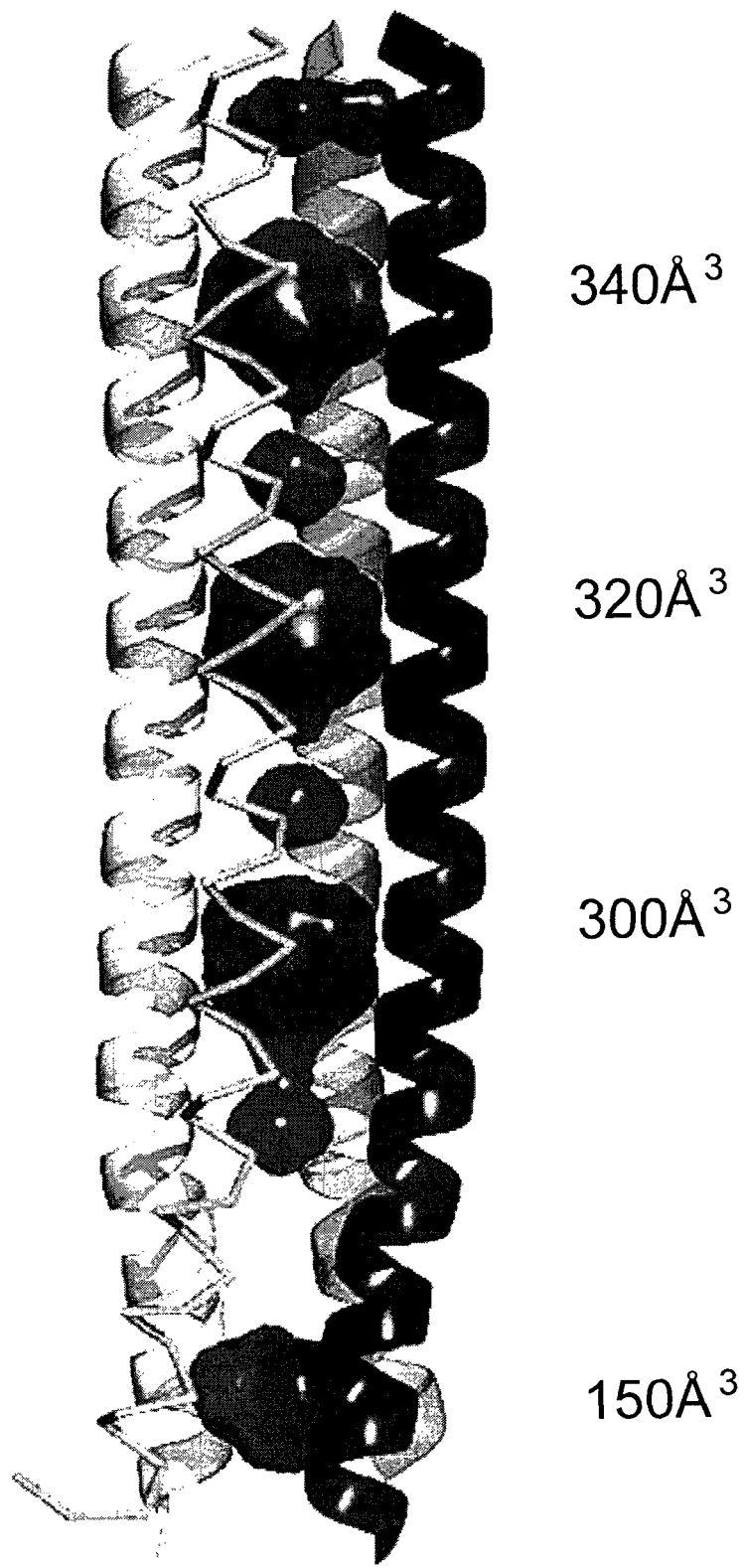
FIG. 7 shows an exemplary crystal structure of the RHCC polypeptide chain fragment of tetrabrachion, illustrating the globular hydrophobic cavities.

The RHCC molecule contains four large globular cavities along the inside of the tetramer (FIG. 6), which have sizes in the range 150 Å$^3$ to 340 Å$^3$. The original X-ray structure of RHCC in the native state revealed that the cavities are occupied by water molecules. Because of the lack of buried polar groups and the resulting weak water-protein interactions, these water molecules are clustered into groups. Clusters of nine water molecules and five water molecules are found in cavities two and three, respectively. Cavity one at the N-terminus and cavity four at the C-terminus are occupied by two water molecules and one water molecule, respectively.

It is to be appreciated by those skilled in the art that a "fragment" of the tetrabrachion protein can be any portion or domain of the full-length tetrabrachion protein and may be, but is not limited to, the 52 amino acid residue of the RHCC structure of the tetrabrachion protein. The amino acid sequence of full-length tetrabrachion protein is known (Genbank Accession No. AAC44118), and is described as SEQ ID NO: 1 in the present disclosure. Therefore, a person skilled in the art would understand that the present disclosure contemplates the full-length amino acid sequence of SEQ ID NO: 1 (see FIG. 4) or any portion or domain of the full-length amino acid sequence.

In an aspect of the present disclosure, a use of tetrabrachion protein or a fragment thereof from *Staphylothermus marinus* for recovering a chemical element from a solution and/or suspension is provided.

It is to be understood that tetrabrachion protein and fragments thereof can be made using a variety of cell production systems, such as, but not limited to, mammalian cells, insect cells, yeast, for example, *Saccharomyces cerevisiae*, and bacteria such as but not limited to *Escherichia coli*, *Bacillus subtilis* or *Pseudomonas aeruginosa*.

If desired, the codons of the nucleotide sequence encoding tetrabrachion or a fragment thereof may be optimized for the host cell expressing the construct.

Transformation of a suitable host cell are well known in the art (for example, Maniatis et al, 1982, Molecular Cloning: A Laboratory Manual, Cold Spring Harbor, or Ausubel, et al. (eds), 1989, *Current Protocols in Molecular Biology*, Vol. 1, Green Publishing Associates, Inc., and John Wiley & Sons, Inc., New York) and can be accomplished by a variety of means well described in the art such as transfection, calcium chloride or other chemically induced transformation or electroporation. Regardless of the transformation method, once a modified host cell is generated it can be cultured and the tetrabrachion protein or fragment thereof can be expressed and isolated. In an alternative embodiment, the host cell expressing the tetrabrachion protein or fragment thereof can be used directly for detection and/or recovery of a chemical element from a solution and/or suspension as will be described in more detail below.

In another aspect of the present disclosure, a use of a composition comprising tetrabrachion protein or a fragment thereof from *Staphylothermus marinus* and a carrier therefor for recovering detection and/or recovery of a chemical element from a solution and/or suspension is provided. As used herein, the "carrier" may be, without limitation, a host cell, such as *Saccharomyces cerevisiae* or *Escherichia coli*, or a gel, matrix or other type of attachment surface. Furthermore, the composition of the present disclosure may comprise nanotubes composed of tetrabrachion protein or fragments thereof for detection and/or recovery of chemical elements from solutions and/or suspensions.

In another aspect of the present disclosure, a method for recovering detection and/or recovery of a chemical element from a solution and/or suspension using tetrabrachion protein or a fragment thereof is provided. The method comprises: (a) introducing *S. marinus* or tetrabrachion protein or a fragment thereof from *S. marinus* or a composition comprising tetrabrachion protein or a fragment thereof from *S. marinus* into a solution; and (b) providing conditions that permit the tetrabrachion protein or the fragment thereof to detect and/or recover of the chemical element from a solution and/or suspension. In the step of introducing (a), where tetrabrachion protein or a fragment thereof from *S. marinus* is introduced into the solution or suspension, the tetrabrachion protein or fragment thereof that is introduced can be made as described above. It is optional to express the tetrabrachion protein or a fragment thereof more than once, for example two times or three times, before introducing the expressed tetrabrachion protein or a fragment thereof into the solution or suspension.

In accordance with a further aspect of the present disclosure, there is provided a method for detecting and/or recovering a chemical element from a solution and/or a suspension, wherein, in place of *S. marinus*, a different host cell transformed with a nucleic acid construct encoding tetrabrachion protein or a fragment thereof is introduced into the solution. Accordingly, there is provided a method for recovering sulfur from a solution, wherein the method comprises: (a) introducing a nucleic acid construct encoding tetrabrachion protein or a fragment thereof into a host cell; (b) incubating the host cell under conditions that permit expression of the nucleic acid construct, thereby producing tetrabrachion protein or the fragment thereof; (c) introducing the host cell into the solution or suspension; and (d) providing conditions that permit the tetrabrachion protein or fragment thereof to detect and/or recover the chemical element from the solution and/or suspension.

As provided above, if desired, the codons of the nucleotide sequence encoding tetrabrachion or a fragment thereof may be optimized for the host cell expressing the nucleic acid construct.

In one embodiment, the nucleic acid construct encoding tetrabrachion protein or a fragment thereof may comprise a nucleotide sequence encoding tetrabrachion or a portion thereof operatively linked to a regulatory region. In an exemplary embodiment, the nucleotide sequence may be the sequence according to SEQ ID NO: 3 (see FIG. 8), encoding the 52 amino acid residue sequence (SEQ ID NO: 2) (FIG. 5) of the RHCC structure of tetrabrachion, which is codon optimized for expression in *Escherichia coli*. In an alternative embodiment, the nucleotide sequence may be a codon optimized sequence that encodes the full-length tetrabrachion protein according to the amino acid sequence of SEQ ID NO: 1 (see FIG. 4).

The nucleic acid construct of the present disclosure may be expressed in any suitable host cell that is transformed by the nucleotide sequence, or nucleic acid constructs, of the present disclosure. Examples of suitable host cells include, but are not limited to, bacterial cells such as *Escherichia* sp., *Pseudomonas* spp., *Bacillus* sp., yeast, such as *Saccharomyces* sp., *Schizosaccharomyces* sp. and *Candida* sp.

Recovery of sulfur from solutions, such as organic liquids, waste water, mine tailings, oils, coal and effluents of various processes containing sulfur is important for reducing damage to both the natural environment as well as to man-made environments. Furthermore, any recovered sulfur or sulfur-containing compounds can be used for various applications, such as the manufacture of cellophane and rayon, as a component of fertilizers, in pharmaceuticals, dyestuffs and agrochemicals, as a fungicide or pesticide and in the fermentation of wine.

The inventors have found that it is more thermodynamically favourable for $S_8$, the most common allotrope of sulfur, and $S_{10}$, another allotrope of sulfur, to occupy the largest hydrophobic cavity of the RHCC structure of tetrabrachion relative to nine water molecules. Furthermore, in freeze-etching cuts of reconstituted S-layers from *S. marinus*, the S-layers showed a strong red coloring after addition of ruthenium, suggesting that the S-layer of tetrabrachion is a storage space for elemental sulphur.

Accordingly, the present disclosure provides uses and methods using tetrabrachion protein or a fragment thereof from *Staphylothermus marinus* for recovering sulfur from a solution or suspension such as those exemplified by any organic liquid, waste water, mine tailings, oils, coal and effluents of various processes. Accordingly, the present disclosure can be applied to any type of application wherein sulfur is to be recovered. For example, without limitation, the present disclosure can be used in relation to the detection and/or recovery of sulfur from any type of industrial application, such as waste water, coal slurries or sludge, petroleum, oil or gas.

Surprisingly, the inventors have also discovered that the tetrabrachion protein or a fragment thereof from *Staphylo-*

*thermus marinus* disclosed herein are also useful for detection and recovery of gold (Au), silver (Ag), platinum (Pt), mercury (Hg), copper (Cu), and other such chemical elements from solutions and suspensions using the methods disclosed herein. Accordingly, the present disclosure can also be applied to any type of application wherein chemical elements exemplified by gold, silver, platinum, mercury, copper, zinc, nickel, tin, lead, and the like are to be detected and/or recovered. For example, without limitation, the present disclosure can be used in relation to the detection and/or recovery of chemical elements from waste water and/or slurries produced during recovery and processing of mineral ores, mine tailings and sludges from tailings ponds, from waste solutions recovered from other types of industrial processes, and from waste solutions recovered after administration of medical procedures.

The present disclosure will be further elaborated in the following examples. However, it is to be understood that these examples are for illustrative purposes only, and should not be used to limit the scope of the present disclosure in any manner.

EXAMPLES

Example 1: Incorporation of Sulphur into a Crystallisable RHCC Compound

Calculation of Free Energy Difference

Central to understanding the preference of a protein cavity, such as those found in the RHCC domain of tetrabrachion, to bind one particular ligand over another is a determination of the free energy difference between two thermodynamic states. In this study, a free energy perturbation (FEP) methodology was used to determine $\Delta(\Delta G)$, the difference between the binding free energy of two different ligands in a given active site. In particular, an application of the PEP methodology reported by Helms and Wade (1995, *Thermodynamics of water mediating protein-ligand interactions in cytochrome P450cam: a molecular dynamics study*. Biophys. J. 69(3):810-24) was used to calculate the free energy for exchanging an $S_8$ allotrope of sulfur or an $S_{10}$ allotrope of sulfur with nine water molecules in the largest cavity (340 Å$^3$ in size) of the RHCC polypeptide chain fragment of tetrabrachion from *S. marinus*. A person skilled in the art would understand that any method for calculating the free energy difference may be used.

In this study, the absolute binding free energy of $S_8$ and $S_{10}$ to the RHCC polypeptide chain fragment of tetrabrachion from *S. marinus* was calculated. A crystal structure of a portion of the RHCC domain with a symmetric cluster of nine water molecules is shown in FIG. 9(A), and a crystal structure of a portion of the RHCC domain with a highly ordered S8 sulfur cluster is shown in FIG. 9(A). FIGS. 10(A)-10(C) show model calculations of the water molecules (10(A)) and the $S_8$ sulfur cluster (10(B)) and $S_{10}$ sulfur cluster (10(C)) in the largest cavity, of the RHCC domain.

Free energy is used as a measure of the relative stability of a system, that is, the tendency of the system to react or change. If the change in free energy, $\Delta G$, is negative, the transformation of the system will occur spontaneously, since transitions in which the energy decreases are favoured, whereas, those in which the change in free energy, $\Delta G$, increases are not favoured.

As shown in FIGS. 10(A)-10(C), the change in binding free energy of an $S_8$ sulfur cluster in the largest cavity of the RHCC polypeptide chain fragment is $\Delta G=-84$ kJ/mol and the change in binding free energy of a $S_{10}$ sulfur cluster in the largest cavity of the RHCC polypeptide chain fragment is $\Delta G=-58$ kJ/mol, both of which are more negative than that for nine water molecules ($\Delta G=-34$ kJ/mol). These exemplary embodiments therefore indicate an energetic preference for tetrabrachion to bind sulfur over water molecules.

Initial Octylglucoside Suitability Assay

For incubation with RHCC, a suitable detergent that solubilises S would have to move freely through a dialysis membrane. N-Octyl β-D-glucopyranoside (OG) with a CMC of 0.53% was found to solubilise ~100 uM of $S_8$ at a 5% detergent concentration in a 10 mM Tris I=154 mM pH=8 buffer. Concentrations of $S_8$ were estimated based on molar extinction coefficients of $S_8$ in methanol and methylcyclohexane, which were later found to be unreliable due to suspected impurities in the sublimed sulfur sample. OG micelles were clearly visible with DLS, and were almost completely gone after an overnight dialysis in a GABAflextube with a MWCO of 3500 Da.

Octylglucoside Incubation with RHCC

Two mg of RHCC was added to 4 mL of 5% OG saturated with S for a final protein concentration of 0.5 mg/mL. The solution was allowed to mix for 9 days, and then dialysed for 5 days in a 10 mM Tris I=154 mM pH=8 buffer. The UV-Vis of the resulting solution was positive for S. However, a DLS measurement yielded a particle $r_h$ of 20.6 nm, while the expected hydrodynamic radius for the RHCC tetramer is 2.7 nm. The solution was then dialysed for 15 days at 60° C., but DLS showed no change in the particle size. The sample was then run through the FPLC, and the elution volume of the sample was identical to the RHCC tetramer. DLS readings taken 15 minutes after elution, however, showed the particle size unchanged.

Subsequently, the protein alone was incubated in the presence of a high excess of insolubilized sublimed sulfur at 80° C. The reported solubility of pure $S_8$ in water was reported to be 5 μg/L. However, absorbance values of the sublimed sulfur in pure water were far too high. This suggested other sulfur species, such as semi-soluble polysulfur anions were also present in the sublimed sulfur. As the elemental sulfur bond absorbs in a similar fashion for all inorganic sulfur species, the absorbance of sulfur could be mathematically treated as the absorbance of one compound with unknown extinction coefficient $\epsilon(S)$. As such, the absorbance of the solution containing both RHCC and sulfur could be expressed by the following:

$$\text{Abs(solution}=\text{Abs(RHCC)}+\text{Abs}(S)=\epsilon(\text{RHCC})\cdot b\cdot c\text{RHCC}+\epsilon(S)\cdot b\cdot c(S) \quad \text{Eq 1}$$

where $\epsilon(\text{RHCC})$ is the extinction coefficient of RHCC in M$^{-1}$ cm$^{-1}$, b is path length in cm, and c(RHCC/S) are the concentrations of RHCC and S in M. The RHCC control and sulfur control were incubated in the same conditions as the RHCC-S solution, and if no interaction took place between the two, the relationship $$\text{Abs(solution)}=\text{Abs(RHCC)control}+\text{Abs}(S\text{ control}) \quad \text{Eq 2}$$

would hold true. Experimentally, this expression did not hold, indicating that sulfur interaction with RHCC caused more sulfur to enter solution. If we assume that RHCC binds S stoichiometrically, we can define an RHCC-S complex where $$\text{Abs(RHCC-}S\text{)}=\text{Abs(solution)}-\text{Abs}(S\text{ control})=\epsilon(\text{RHCC-}S)\cdot b\cdot c(\text{RHC-}S) \quad \text{Eq 3}$$

If the complex is stable, dialysis of the solution would change the concentration, but not the extinction coefficient, and $$\frac{abs(solution) - abs(control)}{abs(dialysis\ product)} = \frac{Abs(RHCC - S1)}{Abs(RHCC - S2)} = \quad \text{Eq 4}$$

$$\frac{\varepsilon(RHCC - S)\, b\, c1(RHCC - S)}{\varepsilon(RHCC - S)\, b\, c2(RHCC - S)} = \frac{c1(RHCC - S)}{c2(RHCC - S)} = \text{constant}$$

would hold true for all wavelengths. Indeed, in the range of measurable sulfur/RHCC absorbances, this does hold true. The sulfur incubation was repeated in different buffers with different pHs to eliminate other sulfur reactions as the cause of the complex formation, and it was found that the complex forms under both acidic and basic conditions. It was found RHCC alone incubated in MES with a pH=6 at 80° C. fully degraded, while the sulfur-containing solution fared much better, with mass spectrometry indicating only some RHCC monomers had lost the N- or C-terminal residue. At this time, the purified RHCC-S complex was crystallized. Protein crystals were grown by hanging drop vapour diffusion over a reservoir composed of 1.5 M ammonium sulfate, 100 mM Tris buffer, pH=8-0 at 4° C. Drops were composed of equal amounts of protein and reservoir solutions. Colourless crystals grew within 5 days and were soaked in 30% glycerol (v/v) cryoprotectant prepared from mother liquor immediately prior to data collection. Data was collected at 100K on a Rigaku R-AXIS VI++ detector with a MicroMax HF generator. Reflections were integrated with MOSFLM (http://www.mrc-lmb.cam.ac.uk/harry/mosflm/; this domain is owned by the Medical Research Council, Laboratory or Molecular Biology, Cambridge Biomedical Campus, Cambridge CB2 0QH, England), scaled and merged with SCALA (http://www.scala-lang.org/; this domain is owned by École Polytechnique Fédérale, Lausanne (EPFL) Lausanne, Switzerland), and converted to amplitudes with TRUNCATE (http://www.ccp4.ac.uk/html/truncate.html; this domain is administered by CCP4 Research Complex at Harwell (RcaH), STFC Rutherford Appleton Laboratory, Harwell Science and Innovation Campus, Didcot, Oxon OX11 OFA, United Kingdom) from the CCP4 program suite (http://www.ccp4.ac.uk/; this domain is administered by CCP4 Research Complex at Harwell (RcaH), STFC Rutherford Appleton Laboratory, Harwell Science and Innovation Campus, Didcot, Oxon OX11 OFA, United Kingdom). Phasing was done by molecular replacement with RHCC cocrystallized with CAPB (PDB ID 1ybk) as the search model using rigid body refinement with REFMAC5 (http://www.ccp4.ac.uk/html/refmac5.html; this domain is administered by CCP4 Research Complex at Harwell (RcaH), STFC Rutherford Appleton Laboratory, Harwell Science and Innovation Campus, Didcot, Oxon OX11 OFA, United Kingdom).

Example 2: An Exemplary Expression and Purification of RHCC

Preparation of RHCC Vector

A synthetic gene encoding the 52 amino acid residue RHCC domain of tetrabrachion from *Staphylothermus marinus* (see FIG. 8) was cloned into the vector pET15b (Novagen) at the BamH1 and EcoR1 restriction sites according to manufacturer's instructions to form the construct pET15b-RHCC. The vector encodes an N-terminal His$_6$-tag to aid in the purification of RHCC by affinity chromatography following the method taught by Porath et al. (1975, *Metal chelate affinity chromatography, a new approach to protein fractionation*. Nature 258: 598-599) and a thrombin cleavage site that enables the cleavage of the His-tag residue after purification. Expression of the target protein is under the control of the T7 promoter which is IPTG inducible. The gene that encodes for the antibiotic resistance for the plasmid is ampicillin.

Preparation of RHCC Plasmid Stock

A 1-μl aliquot of a pre-existing 100 μg/ml pET15b-RHCC plasmid stock was added to 100 μl of calcium chloride competent DH5α cells. The plasmid was incubated with the cells on ice for 30 minutes. Then the mixture was incubated for 90 seconds at 42° C. (heat shock) before being placed back on ice for another 30 seconds. After the heat hours at 37° C. The mixture was pelleted in a microcentrifuge at 4,000×g for 1 minute to remove the excess LB broth. The pellet was resuspended in the residual LB broth, with the transformation plated out onto LB/Amp plates and incubated overnight at 37° C.

A single colony of DH5a cells transformed with pEt15b-RHCC was picked and transferred into 5 ml LB/Amp. The plasmid-containing cells were grown up overnight at 37° C. before purification of the plasmid DNA according to the QIAGEN® mini-prep protocol (QIAGEN is a registered trademark of Qiagen Gmbh, Hilden, Fed. Rep. Germany). The freshly prepared pET15b-RHCC plasmid stock was stored at −20° C.

Bacterial Growth and Expression of Recombinant RHCC Protein

Competent *E. coli* cells (50 μl) of strain BL21(DE3) were transformed with a 1 μl aliquot of the pET15b-RHCC plasmid stock (100 μg/ml) following the method disclosed by Studier et al. (1990, Use of T7 RNA polymerase to direct expression of cloned genes. Methods Enzymol. 185:60-89). The mixture was kept on ice for 30 minutes and then the cells were heated to 42° C. for 90 seconds before placing back on ice. After the heat shock, 100 μl LB broth was added to the cells and incubated at 37° C. for 30 minutes. The transformed cells were plated out onto LB plates containing 100 μg/ml ampicillin and incubated overnight at 37° C.

Pre-cultures were grown by inoculating 50 ml of LB/Amp media with a single colony of BL21/(DE3) transformed with pET15b-RHCC and incubated at 37° C. overnight in a shaker (200 rpm). To 1.6 L of fresh LB/Amp media, 20 ml of pre-culture was added and the cells were allowed to grow to an OD600 of 0.6 at 37° C. with shaking. The cells were induced by adding Isopropyl β-D-1-thiogalactopyranoside (IPTG) to a final concentration of 1 mM. Bacteria cell cultures were kept in the shaker and left to express the RHCC protein for 3 hours. Then the cells were harvested by centrifugation at 6,000×g for 20 minutes at 4° C. The LB supernatant was discarded and cell pellets were stored at −20° C.

Purification of the RHCC Protein

The bacterial cell pellets from the 1.6 L expression culture was resuspended in 30 ml Binding buffer (20 mM Tris-Cl, pH 7.5, 5 mM Imidazole, 500 mM NaCl, 8 M Urea) and kept on ice. The cells were lysed by three passages through a French Pressure Cell (SLM Instruments, Urbana Ill., U.S.A.). Unlysed cells and cell debris were removed by centrifugation using a Beckman JA 25.50 rotor (Beckman-Coulter Centrifuge, U.S.A.) at 20,000×g for 20 minutes at 4° C. Production and purification of the His6-tagged RHCC fusion protein was performed at room temperature by affinity chromatography on Ni2+-Sepharose (GE Healthcare) under denaturing conditions disclosed by Stetefeld et al.

(2000, *Crystal structure of a naturally occurring parallel right-handed coiled coil tetramer*. Nat. Struct. Biol. 7:772-776).

Separation of the RHCC polypeptide chain fragment from the His6-tag was achieved by using biotinylated thrombin, according to the manufacturer's instruction (EMD Biosciences Inc.). This is possible as the pET15b vector encodes a thrombin cleavage site between the His6-tag and the N-terminus of the expressed protein (see FIG. 8). Aliquots of the protein sample were incubated for 2, 4, 8 and 16 hours at room temperature to identify the optimal cleavage conditions. The cleavage reaction was stopped by a 10-min incubation of the reaction mix at 90° C. in a water bath. After the heat inactivation step, the biotinylated thrombin was removed from the sample by passing the thrombin/RHCC mixture over a streptavidin agarose column according to the manufacturer's protocol (EMB Biosciences Inc.). To ensure the complete removal of the thrombin from the sample, 32 μl of streptavidin slurry was required per unit of the thrombin protease used. The RHCC polypeptide chain fragment contains two additional N-terminal Gly and Ser residues that originate from the expression plasmid and are not part of the tetrabrachion coding sequence.

Example 3: An Exemplary Expression and Purification of RHCC

The RHCC-His6 gene, which contains a thrombin cleavage site, was inserted into a pET-15b vector, which was then transformed into an *E. coli* strain BL21/DE3. These cells were grown in LB broth, then spun down and the pellet collected and frozen at −70° C. These frozen cells form the stock that was used to purify the RHCC used in this project. To begin RHCC expression, some of the stock cells are inoculated into 50 mL of LB broth with an ampicillin concentration of 0.1 mg/mL. This pre-culture is allowed to grow for 12-16 hours, then added to 1.8 L of LB broth, again with a 0.1 mg/mL ampicillin concentration. These cells are allowed grow to an optical density of 0.6 before protein expression is induced with 0.8 mL of 1 M IPTG. This culture grows for 3 hours before it is centrifuged at 6000 rpm at 4° C. for 20 minutes with an Avanti J26-XPI centrifuge with a JLA 8.100 rotor and the cell pellet collected. The cells are resuspended in a 20-mM phosphate buffer at pH 7 containing 2 mM imidazole and 6M guanidine hydrochloride. The guanidine begins denaturing the cellular proteins, causing many to precipitate out of solution. The cells are then lysed with a Dounce tissue grinder, and then sonicated to complete cell lysis and shear DNA. This solution is centrifuged at 20500 rpm at 4° C. for 30 minutes in a JA 25.50 rotor and the pellet is discarded. This removes much of the cellular debris, such as the membrane and precipitated proteins. The 6 terminal His residues on the recombinant RHCC interact strongly with divalent metal ions, such as nickel or cobalt. Thus, the unpurified protein solution is run through a Talon cobalt affinity column, and the final purified RHCC-His6 is eluted with a 150-mM imidazole solution. The protein concentration of the eluent is approximated by UV-Vis (imidazole absorbs strongly at 280 nm, where the Tyr residues of RHCC also absorb), and 1μ of thrombin is added for each mg of RHCC-His6. This solution is contained in a dialyses tube with a MWCO of 3500 Da. This pore size allows the cleaved His tag to move into the extraneous buffer (20 mM Tris, I=154 mM NaCl, pH=8) while containing the thrombin and the RHCC. As the thrombin cleavage is quite slow, the solution buffer is changed 3 times over the course of a week. The progress of the thrombin cleavage is checked via SDS-PAGE. The thrombin and any remaining His tag is then removed with a benzamidine affinity column. Benzamadine is specific for serine proteases such as thrombin. However, RHCC interacts strongly enough to the column to require elution via a high salt wash (20 mM Tris I=1M NaCl, pH=8), thus, separation from any remaining His tag in solution is achieved. The final protein solution is then concentrated to 10 mg/mL, dialysed to a 10 mM Tris I=154 mM pH=8 buffer, then analysed with FPLC and DLS to confirm purity and integrity of the protein.

Example 4: Use of RHCC for Sequestration of Gold

Figure 11:
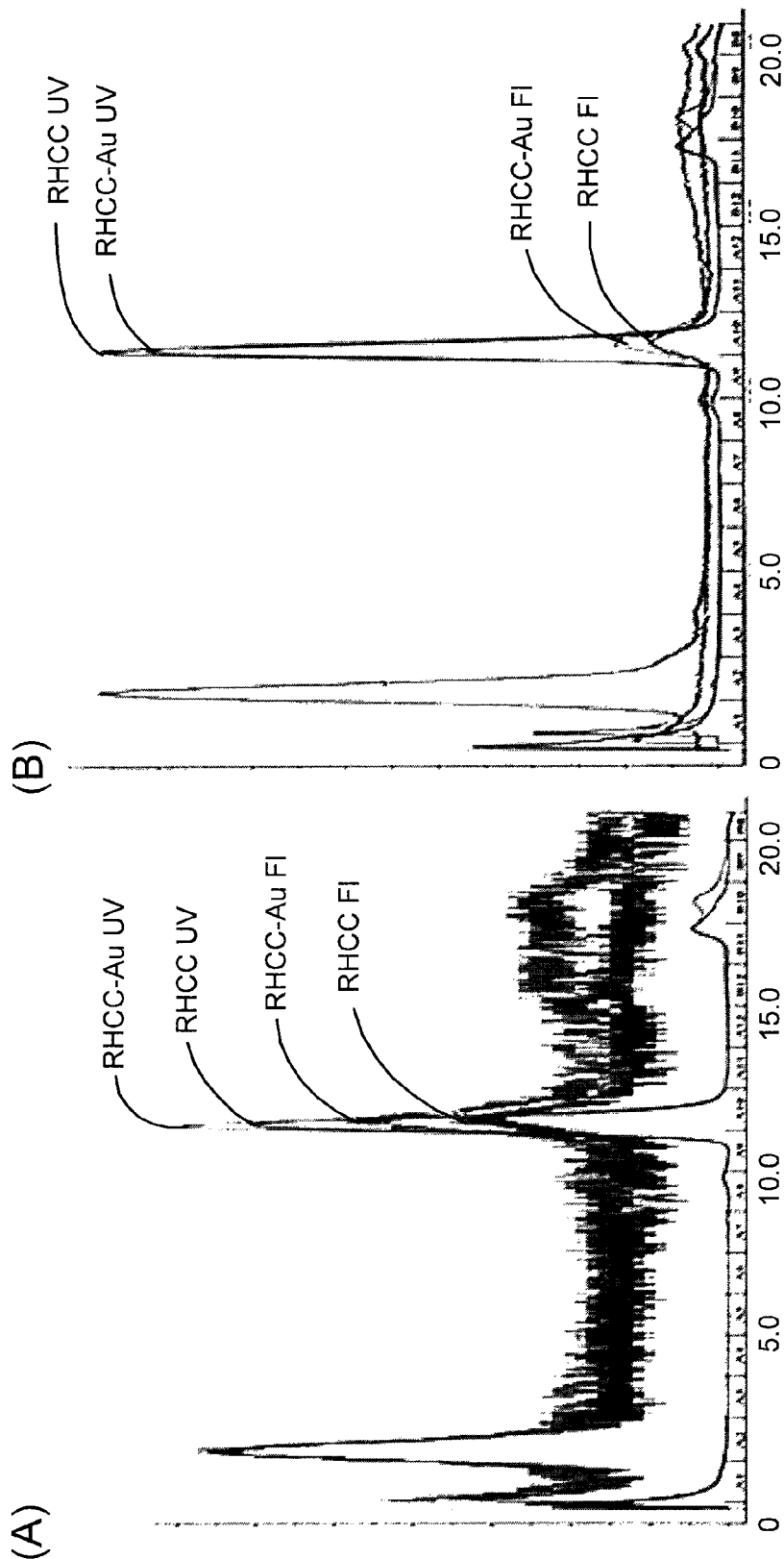
FIGS. 11(A)-11(D) are charts showing the results of Fast Protein Liquid Chromatography (FPLC) of RHCC-Au with Fluorescence (11(A)) and UV Detection (11(B))

The potential use of the RHCC produced as described herein, for capture and sequestration of metal ions was assessed. Initial screening studies indicated that RHCC could bind metal ions in solution, specifically $Hg^{2+}$. The data suggested that metal nanoparticles in the cavities of the RHCC protein might have catalytic functionality and that the dimensions of the cavity would impose size restrictions on the reactants which would be very attractive in organic synthesis. Crystallographic data from mercury soak experiments also suggest that the mercury exists in a reduced state, as there is a lack of interaction with the peptide backbone or acidic residues, and it is only found inside the hydrophobic cavities. Therefore the first step in the preparation of $Au^0$-RHCC compounds was to confirm that RHCC is indeed capable of reducing metal ions. The chosen technique for detection of reduction of metals was XPS. XPS is a technique that measures the kinetic energy of electrons that fly off of a solid sample that is bombarded by Xrays. This yields information about the composition of the sample, including the oxidation states of all of the elements. XPS can also be used to determine the stoichiometry of elements present in the sample; however, buffer components prevented the use of XPS to determine the number of bound metals in this study. Assays were conducted with $K_2PtCl_4$, $Hg(NO_3)_2$, $K_2HgI_4$, $CuCl_2$, $KAuCl_4$, and $KAu(CN)_2$. Definitive reductions were seen with $CuCl_2$, $Hg(NO_3)_2$, and $KAuCl_4$. $CuCl_2$ was chosen specifically due to a 'shake-up' peak in the XPS spectrum that disappears after reduction. Visible reduction was seen in the case of $KAuCl_4$ in the form of purple nanoparticles. However, for the purple color to develop, the nanoparticle must be >80 nm in diameter, which is far too large to fit in the cavity. However, this purple coloration proved an easy way to test for reduction in solution under different conditions without lyophilisation and XPS analysis. Dynamic Light Scattering (DLS), which measures the hydrodynamic radius of a particle in solution, showed the resulting particles were all much larger than the original RHCC tetramer, indicating extensive aggregation. Crystal formation for X-ray diffraction analysis requires a pure compound, and aggregation would negatively affect crystal growth. It was noted that the purple coloration in the $KAuCl_4$ solution only appeared after dialysis. We postulated that the reduction reaction is pH dependant, and in further trials in basic conditions, $KAuCl_4$ and $KAu(CN)_2$ were reduced without dialysis. Small gold clusters have unique optical properties, with fluorescent excitation and emission wavelengths sharply defined and dependant solely on the size of the cluster and the intensity of the fluorescence dependant on the concentration of the cluster. An FPLC outfitted with both fluorescent and UV-Vis detectors was used to monitor for the presence of small gold clusters and protein simultaneously, and the peaks overlapped, suggesting RHCC complexed with the gold cluster. The fluorometer was set to measure $\lambda_{ex}$=385 nm, $\lambda_{em}$=455 nm for $Au_8$ clusters and $\lambda_{ex}$=434 nm, $\lambda_{em}$=510 nm for $Au_{13}$. The fluorometer was unable to measure $\lambda_{ex}$=330 nm, $\lambda_{em}$=385 nm for $Au_5$. The UV-Vis detector was set to measure at 280 nm for protein absorbance. The $\epsilon_{280}$ for the RHCC monomer is 2980 $M^{-1}$ $cm^{-1}$. It was found that the ratio of peak heights Fluorescence:$Abs_{280}$ was roughly equal with and without the presence of gold when monitoring fluorescence for $Au_{13}$, while the fluorescence peak when scanning for $Au_8$ was markedly higher than in the control (FIGS. 11(A), 11(B)). The cavities in RHCC and its reductive properties make it possible for loading gold in a regular manner relatively easy to do. The data collected using X-ray Photoelectron Spectroscopy (XPS) demonstrate that RHCC can reduce gold salts in solution, and Fast Protein Liquid Chromatography (FPLC) with a fluorescence detector indicates that gold clusters are incorporated into the structure of RHCC (FIGS. 11(A), 11(B)).

There are three amino acids implicated in gold reduction; cysteine, histidine, and tyrosine. However, there are no cysteine or histidine residues present in RHCC, and four tyrosine residues line the largest cavity. Tyrosine-dependant gold reduction proceeds through the formation of a tyrosyl intermediate, with the neutralization of one positive charge. Though accounts vary one the resolution of the intermediate, it seems likely that a high excess of metal ions would lead to the tyrosine donating the radical to another metal. Thus, the tyrosine lined cavity would be able to reduce a total of eight positive charges. The physical chemical jellium model predicts fluorescence of certain cluster sizes based on the electronic configuration of the cluster. The smallest stable gold clusters are $Au_5$, $Au_8$, and $Au_{13}$, and each have distinct fluorescent properties that allow detection of fluorescence. The FPLC separation of the Au-RHCC indicated that $Au_8$ is most likely present. An FPLC separation after one week with the reactants sitting at room temperature resulted in a flat line UV chromatogram, but the fluorometer measured $Au_8$ elution at the volume expected for RHCC elution. SDS-PAGE of the solution showed no protein degradation. This supports the theory that the Tyr residues are responsible for gold reduction, as Tyr is the only absorbing species present in RHCC. In addition, RHCC contains no amino acid residues capable of covalently binding gold cluster, thus for the Au to elute with RHCC it must be incorporated into the quaternary structure of the protein. It is interesting to note that the reduction of $KAu(CN)_2$ in extremely basic conditions proceeded without the evolution of purple coloration caused by unprotected gold cluster aggregation. Therefore it seems the $Au_8$ is protected by some size limiting structure. In other syntheses, these small gold particles are protected by massive dendrimers. There is no evidence for such particles forming from buffer constituents or multiple RHCC tetramers by DLS or FPLC analysis. This again suggests the Au cluster is contained and protected by the protein tetramer.

Example 5: Incorporation of Metal Cations by RHCC

Metal Soak Experiments

RHCC stock solutions from Example 1 were combined and dialysed into a 10 mM Tris I=154 mM pH=8 buffer. This new solution was determined by UV-Vis (WPA Biowave II UV-Vis Spectrophotometer) to be 10.1 mg/mL. The solution was subjected to Sodium Dodecyl Sulfate Polyacrylamide Gel Electrophoresis (SDS-PAGE), DLS (Zetasizer Nano-S in a 3 mm quartz cuvette) and FPLC (AKTA setup with a GE Superdex 75 gel filtration column) analyses to ensure no degradation of the protein had taken place. For the initial metal soak experiments, 0.1 M solutions of $Hg(NO_3)_2$, $CuCl_2$, $KAuCl_4$, and $K_2HgI_4$ were prepared, and 50 uL of these solutions were added to 493 uL of 10.1 mg/mL RHCC and diluted with 457 uL for a final concentration of 5 mg/mL RHCC, and 5 μM metal salt. Solutions were allowed to soak for 2 days, and then dialysed for 2-7 days to remove any uncomplexed metal salts. The resulting solutions were then lyophilized, and analyzed by X-ray Photoelectron Spectroscopy (XPS). These experiments were then repeated with K2PtCl4, K2Pt(CN)4 and KAu(CN)2 from newly purified RHCC.

Refined $KAuCl_4$ Experiment

RHCC was dialysed into a 10-mM bicine, I=154 mM (NaCl), pH=8 buffer. This was done because Tris buffer interferes with the double-junction pH electrode. FPLC and DLS measurements confirmed the stability of RHCC in this buffer. 2 mL of 3 mg/mL RHCC solution was used to ensure adequate volume for pH measurements with the VWR symphony pH meter, using a VWR symphony electrode model 14002-784. A parallel control without RHCC was also run to exclude the buffer as the reductive element. 10 uL of 50 μM $KAuCl_4$ were added to the tubes, and the pH monitored. A UV-Vis spectrum was taken every 15 minutes. After 30 minutes with no change, the pH was adjusted to 8.6 with 1 M NaOH. After a further 15 minutes with no visible change, 10 μL of $KAuCl_4$ solution were added to both solutions. After 45 minutes, a purple colour was observed, but the colour change was not accompanied by a measurable change in pH. DLS measurements showed a smaller particle than the initial RHCC, which resolved with time into a particle with an rh equal to that of the tetramer. FPLC analysis showed 4 distinct particles, one at the same elution volume of pure RHCC.$KAu(CN)_2$ reduction.

$KAu(CN)_2$ was added in a 50:1 molar ratio to RHCC tetramer in 10-mM bicine, I=154 mM (NaCl), and the pH was adjusted to 11. The solution was left overnight, and then was separated by FPLC with a Sephadex 75 column in tandem with a Jasco FP-2020 Plus fluorometer, monitoring at $\lambda_{ex}$=385 nm, $\lambda_{em}$=455 nm for $Au_8$ clusters and $\lambda_{ex}$=434 nm, $\lambda_{em}$=510 nm for $Au_{13}$. These chromatogram profiles indicate RHCC is bound to elemental gold clusters.

Example 6: The Incorporation of Hydrogen Sulfide by RHCC

Hydrogen sulfide gas was prepared by reacting Iron (II) Sulfide powder with concentrated hydrochloric acid. The gas was collected in a syringe and bubbled through a solution of 10.1 mg/mL RHCC. The solution was kept in an airtight container overnight before crystallization. Protein crystals were grown by hanging drop vapour diffusion over a reservoir composed of 1.5 M ammonium sulfate, 100 mM Tris buffer, pH=8.0 at 4° C. Drops were composed of equal amounts of protein and reservoir solutions. Colourless crystals grew within 5 days and were soaked in 30% glycerol (v/v) cryoprotectant prepared from mother liquor immediately prior to data collection. Data was collected at 100K on a Rigaku R-AXIS VI++ detector with a MicroMax HF generator. Reflections were integrated with MOSFLM, scaled and merged with SCALA, and converted to amplitudes with TRUNCATE from the CCP4 program suite. Phasing was done by molecular replacement with RHCC cocrystallized with CAPB (PDB ID 1ybk) as the search model using rigid body refinement with REFMAC5 (FIG. 9(C)).

Example 7: Reduction and Binding of Mercury and Copper Salts by RHCC

Figure 12:
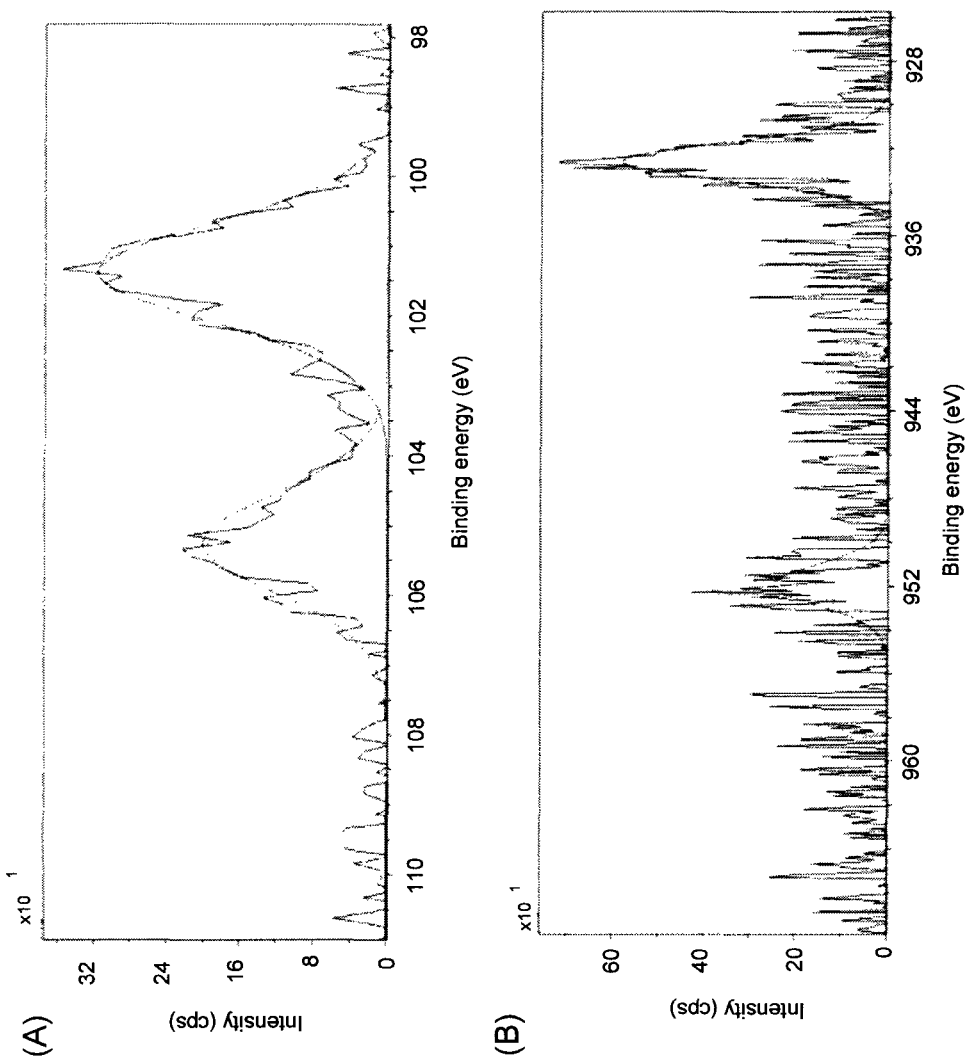
FIGS. 12(A)-12(B) are charts showing X-ray photoelectron spectroscopy (XPS) of mercury bound by RHCC (12(A)) and copper bound by RHCC.

In 10 mM tris buffer, pH 8 I=150 mM (NaCl), 0.1 M Hg(NO$_3$)$_2$ (Hg$^{2+}$) was incubated with 5 mg/mL RHCC for 24 hours. The resulting solution was then dialyzed against 500-fold excess of 10 mM tris buffer, pH 7.5 I=150 mM (NaCl) to completion. in a 3500 MWCO dialysis tube, then changed to fresh buffer and dialyzed to completion once more. The sample was then lyophilized and analyzed by X-ray photoelectron spectroscopy (XPS), which demonstrated that the mercury was reduced by the protein to elemental mercury (FIG. 12 (A)). An identical assay was conducted with CuCl$_2$ (Cu$^{2+}$) and it was found that copper was likewise reduced (FIG. 12(B)). As the membrane of the dialysis tube would be permeable to small Hg and Cu clusters, their presence in the final dried sample suggests RHCC is capable of sequestering these metals.

---

What is claimed is:

1. A composition for detecting or recovering a chemical element from a solution or a suspension, the composition comprising; a gene construct encoding a tetrabrachion protein or a tetrabrachion protein fragment thereof, wherein the tetrabrachion protein consists of an amino acid sequence SEQ ID NO: 1 or a tetrabrachion protein fragment consists of an amino acid sequence SEQ NO ID: 2 and a carrier therefor.

2. The composition of claim 1, wherein the chemical element is a sulfur.

3. The composition of claim 1, wherein the chemical element is one or more of gold, silver, platinum, mercury, copper, zinc, nickel, tin, and lead.

* * * * *

SEQUENCE LISTING

```
<160> NUMBER OF SEQ ID NOS: 3

<210> SEQ ID NO 1
<211> LENGTH: 1524
<212> TYPE: PRT
<213> ORGANISM: Staphylothermus marinus
<220> FEATURE:
<221> NAME/KEY: misc_feature
<222> LOCATION: (339)..(339)
<223> OTHER INFORMATION: Xaa can be any naturally occurring amino acid

<400> SEQUENCE: 1

Met Asn Arg Val Leu Ala Tyr Ser Leu Leu Ala Ile Met Thr Leu Ser
1               5                   10                  15

Leu Leu Ile Ile Pro Ala Pro Gly Ile Ala Gln Arg Ile Thr Val Gly
                20                  25                  30

Val Ser Val Lys Ala Gly Thr Tyr Asn Phe Tyr Asn Ile Thr Pro Thr
            35                  40                  45

Thr Gln Thr Val Glu Val Thr Asp Asn Gly Met Leu Arg Val Ile Ile
        50                  55                  60

Asn Arg Thr Glu Ala Thr Glu Leu Gly Thr Thr Ile Arg Leu Ala Phe
65                  70                  75                  80

Ile Leu Asp Thr Asp Lys Tyr Asp Pro Asn Val Gly Gly Tyr Phe Leu
                85                  90                  95

Asn Val Ser Asn Ile Gly Val Tyr Ala Pro Ser Asp Pro Thr Gln Ser
            100                 105                 110

Pro Tyr Gly Gly Val Ile Asp Ile Thr Gln Asn Ser Thr Leu Thr Asp
        115                 120                 125

Gly Thr Gln Val Val Gly Asn Val Thr Val Val Asn Gly Gly Asn Asn
    130                 135                 140

Val Ile Ile Leu Ile Asp Leu Ser Lys Leu Pro Asp Leu Gln Asn Val
145                 150                 155                 160

Val Tyr Ile Thr Asn Val Tyr Thr Glu Thr Ser Thr Thr Ala Asn Leu
                165                 170                 175

Thr Asn Thr Leu Leu Arg Val Lys Ala Phe Asp Ala Ala Ser Trp Asp
            180                 185                 190

Ala Val Ile Ser Gly Asn Gln Phe Lys Ile Leu Tyr Ile Pro Ser Leu
        195                 200                 205

Cys Lys Tyr Val Lys Ile Asn Val Ile His Ser Pro Ala Ile Val Gly
    210                 215                 220

Thr Asn Val Asp Val Ile Val Ser Phe His Lys Tyr Phe Ser Leu Val
225                 230                 235                 240

Gln Ser Ile Ala Gly Val Ser Leu Asp Ile Thr Val Asp Asn Lys Thr
                245                 250                 255

Gln Leu Asn Met Thr Asn Tyr Tyr Asn Ala Thr Glu Asn Tyr Val Leu
            260                 265                 270

Ala Thr Phe Ile Asn Gly Asn Leu Thr Val Gly Gly Ser Glu Val Phe
        275                 280                 285
```

```
Ser Ser Pro Thr Val Thr Val Ile Asn Ala Ser Thr Phe Lys Tyr Ser
    290                 295                 300
Gly Gln Val Lys Asp Tyr Ala Pro Thr Val Ala Asp Thr Ala Thr Pro
305                 310                 315                 320
Trp Val Arg Thr Leu Asn Lys Phe Glu Val Glu Phe Arg His Glu Ile
                325                 330                 335
Val Asn Xaa Thr His Asp Leu Ile Phe Tyr Ile His Cys Asp Ser Asp
            340                 345                 350
Thr Val Ser Tyr Asp Thr Trp Pro Phe Leu Ile Val Asn Ala Ser Leu
        355                 360                 365
Asp Ile Thr Thr Thr Glu Val Ala Phe Asn Ser Thr Thr Ile Asn Pro
370                 375                 380
Gly Asp Ile Val Asn Phe Thr Ala His Asn Val Pro Leu Gln Tyr Leu
385                 390                 395                 400
Thr Ala Thr Asn Tyr Gly Val Leu Arg Phe Gln Leu Ile Asn Pro Ala
                405                 410                 415
Leu Val Val Tyr Val Pro Val Ser Asn Met Thr Leu Ser Ala Asn Thr
            420                 425                 430
Thr Thr Gly Ile Ile Asn Gly Ser Phe Val Leu Pro Asp Ala Pro Tyr
        435                 440                 445
Gly Gly Leu Asp Tyr Leu Thr Tyr Leu Val Phe Asn Asp Gly Lys Phe
450                 455                 460
Ile Ala Asn Gly Tyr Ile Thr Val Ser Pro Cys Ile Glu Thr Tyr Val
465                 470                 475                 480
Leu Thr Asn Thr Ser Ala Tyr Ala Glu Asp Ala Gly Ser Ser Tyr Ile
                485                 490                 495
Gly Arg Phe Val Pro Gly Tyr Thr Ser Val Pro Gly Asp Tyr Ile Val
            500                 505                 510
Ile Lys Gly Tyr Gly Phe Ala Leu Ser Asn Leu Thr Gly Phe Thr Val
        515                 520                 525
Ser Ile Asn Asn Thr Asp Val Ile Leu Asn Ala Thr Tyr Asn Ala
530                 535                 540
Ser Thr Gly Lys Ile Ile Ile Leu Ala Lys Leu Leu Asp Thr Asn Gly
545                 550                 555                 560
Thr Pro Ile Pro Val Gly Ala Gly Phe Ile Arg Val Gly Gln Asn Gly
                565                 570                 575
Thr Thr Asn Ile Ala Tyr Ala Pro Phe Asn Val Thr Arg Asn Ser Gly
            580                 585                 590
Leu Glu Lys Val Leu Phe Asn Pro Arg Trp Phe Tyr Asn Gly Thr Tyr
        595                 600                 605
Tyr Ile Glu His Asp Lys Leu Gly Asp Pro Tyr Leu Tyr Phe Pro Val
610                 615                 620
Asp Tyr Pro Leu Val Asn Asn Thr Phe Thr Thr Glu Met Trp Pro Phe
625                 630                 635                 640
Asn Thr Thr Ile Glu Val Ile Gly Trp Pro Thr Asn Thr Phe Thr Leu
                645                 650                 655
Lys Ala Phe Asn Lys Glu Phe Asn Leu Ser Phe Asn Leu Leu Thr Leu
            660                 665                 670
Ser Leu Thr Asn Gly Tyr Asn Met Thr Asn Leu Tyr Asn Leu Thr Ile
        675                 680                 685
Pro Phe Leu Pro Tyr Gly Asn Tyr Thr Leu Leu Glu Gly Thr Leu Leu
690                 695                 700
```

-continued

```
Ser Val Asn Asn Arg Thr Val Phe Thr Val His Met Gly Ile Asn Val
705                 710                 715                 720

Asp Leu Asp Ser Cys Gly Asn Gly Thr Leu Ser Ile Thr Val Val Gly
            725                 730                 735

Ala Ala Pro Asn Thr Glu Tyr Asn Phe Thr Phe Gly Tyr Gln Val His
        740                 745                 750

Asp Leu Asn Tyr Gly Ile Thr Arg Tyr Ile Ser Pro Gln Trp Asn Gly
    755                 760                 765

Thr Trp Asn Ile Ser Leu Val Thr Asp Ile Tyr Gly Thr Gly Ser Thr
770                 775                 780

Ser Val Pro Leu Ile Thr Leu Tyr Pro Thr Ser Tyr Val Ile Asn Ala
785                 790                 795                 800

Thr Trp Asp Val Ile Thr Trp Leu Arg Leu Ser Gly Ser Gly Thr Leu
            805                 810                 815

Asp Leu Leu Phe Ser Val Asp Val Ser Tyr Asn Gly Phe Thr Asp Asn
        820                 825                 830

Leu Thr Thr Pro Ile Thr Tyr Val Phe Gly Pro Ser Asp Thr Thr Pro
    835                 840                 845

Gly Ser Phe Asn Ile Tyr Val Asn Thr Thr Tyr Asn Val Ser Val Val
850                 855                 860

Arg Val Ala Val Asp Tyr Leu Pro Arg Thr Asn Val Val Ile Ser Val
865                 870                 875                 880

Pro Glu Thr Val Leu Pro Gly Asp Thr Ile Thr Val Gln Ile Phe Pro
            885                 890                 895

His His Asn Glu Val Trp Gly Phe Ile Glu Pro Thr Ala Leu Phe Asp
        900                 905                 910

Glu Asn Gln Leu Leu Gly Trp Tyr Leu Thr Val Arg Leu Val Asp Pro
    915                 920                 925

Leu Ser Asn Thr Val Val Glu Arg Val Ala Gly Tyr Tyr Ala Gly Asn
930                 935                 940

Leu Ile Val Glu Asp Val Asp Gly Asp Gly Asp Asn Glu Val Trp Phe
945                 950                 955                 960

Val Val Asn Leu Thr Ala Pro Leu Val Leu Gly Val Asp Lys Thr Tyr
            965                 970                 975

Arg Val Asp Val Glu Leu Phe Leu Ala Val Leu Asn Pro Ser Ser Asn
        980                 985                 990

Ile Thr Gly Val Thr Ala Val Asp Asn Glu Cys Tyr Val Gln Leu Asp
    995                 1000                1005

Leu Asn Gly Thr Ile Tyr Trp Asn Gly Leu Gly Ser Gly Ile Met
    1010                1015                1020

Leu Gly Gly Asp Gly Gln Ile Val Thr Val Leu Gly Val Leu Glu
    1025                1030                1035

Gly Lys Leu Asp Thr Ile Lys Asp Gly Ile Ala Glu Ile Asn Ala
    1040                1045                1050

Thr Val Asn Asp Ile Asn Thr Tyr Leu Lys Val Asn Val Thr Asp
    1055                1060                1065

Leu Leu Lys Thr Ile Asn Asn Ser Val Val Met Ile Lys Asn Asp
    1070                1075                1080

Thr Ala Thr Leu Ile Ile Gly Gln Ala Glu Ile Lys Ala Lys Leu
    1085                1090                1095

Asp Asp Leu Leu Asn Leu Thr Ser Gln Val Asn Asp Thr Val Thr
    1100                1105                1110

Met Ile Leu Ala Cys Cys Asn Asn Ala Ser Lys Val Leu Asn Arg
```

```
            1115                1120                1125
Met Glu Gly Thr Leu Asn Ser Thr Tyr Thr Gly Val  Leu Asn Val
        1130                1135                1140
Lys Ser Asp Leu Ser Thr Leu Ile Asp Thr Ala Asn  Asn Val Val
        1145                1150                1155
Ile Pro Lys Phe Asn Glu Leu Tyr Asp Asn Val Thr  Val Glu Ile
        1160                1165                1170
Asn Ala Ser Arg Asp Leu Ile Ile Gln Lys Ile Ser  Ser Val Asn
        1175                1180                1185
Asp Ser Leu Thr Thr Ile Ile Ser Ala Gly Phe Asn  Asp Val Glu
        1190                1195                1200
Ala Met Ile Ser Asn Leu Asn Thr Thr Leu Leu Asn  Arg Ile Asp
        1205                1210                1215
Glu Leu Glu Gly Thr Leu Leu Phe Tyr Met Thr Ala  Asn Glu Gln
        1220                1225                1230
Arg Leu Glu Gly Ile Ile Asn Glu Thr Ala Asp Asp  Ile Val Tyr
        1235                1240                1245
Arg Leu Thr Val Ile Ile Asp Asp Arg Tyr Glu Ser  Leu Lys Asn
        1250                1255                1260
Leu Ile Thr Leu Arg Ala Asp Arg Leu Glu Met Ile  Ile Asn Asp
        1265                1270                1275
Asn Val Ser Thr Ile Leu Ala Ser Ile Gly Asn Val  Asn Leu Thr
        1280                1285                1290
Val Phe Asn Lys Leu Asn Asp Leu Glu Ile Glu Leu  Gly Asp Val
        1295                1300                1305
Asn Ala Thr Ile Asn Ala Gly Ile Phe Gln Ile Gln  Ser Asn Leu
        1310                1315                1320
Gly Asn Ala Asn Gln Leu Ile Leu Asp Thr Leu Thr  Ser Ser Lys
        1325                1330                1335
Val Glu Ile Leu Asn Ala Ile Ser Ser Asn Ala Ser  Ala Ile Ser
        1340                1345                1350
Ser Glu Ile His Asn Ala Val Asn Gln Leu Ser Thr  Leu Val Leu
        1355                1360                1365
Gln Val Asn Asp Thr Leu Thr Leu Lys Ile Thr Gly  Glu Ala Asp
        1370                1375                1380
Asn Ile Leu Asn Phe Leu Ser Ser Leu Glu Gly Ser  Met Asn Thr
        1385                1390                1395
Gly Phe Asn Asn Val Thr Ser Thr Leu Ser Ala Val  Glu Asn Asn
        1400                1405                1410
Ile Leu Gly Lys Ile Thr Asp Thr Ser Asn Leu Leu  Ser Ser Lys
        1415                1420                1425
Ile Asp Asn Thr Leu Ser Thr Leu Gln Asp Leu Ile  Thr Ser Thr
        1430                1435                1440
Ser Asn Asp Leu Lys Asn Ser Ile Ser Ser Ala Lys  Asn Asp Ile
        1445                1450                1455
Val Ser Ser Leu Ser Ser Lys Val Asp Ser Ser Thr  Gln Thr Leu
        1460                1465                1470
Ser Thr Lys Leu Asp Asp Leu Lys Ser Ala Gln Glu  Ser Asn Thr
        1475                1480                1485
Asn Ser Ile Asn Asn Asn Ile Met Leu Phe Gly Ala  Ala Ser Leu
        1490                1495                1500
Ile Leu Leu Ile Val Thr Ile Gly Leu Val Gly Tyr  Arg Leu Ile
        1505                1510                1515
```

```
Ala Arg  Arg Arg Val Gly
    1520

<210> SEQ ID NO 2
<211> LENGTH: 52
<212> TYPE: PRT
<213> ORGANISM: Artificial Sequence
<220> FEATURE:
<223> OTHER INFORMATION: RHCC polypeptide chain fragment of
      tetrabrachion

<400> SEQUENCE: 2

Gly Ser Ile Ile Asn Glu Thr Ala Asp Asp Ile Val Tyr Arg Leu Thr
1               5                   10                  15

Val Ile Ile Asp Asp Arg Tyr Glu Ser Leu Lys Asn Leu Ile Thr Leu
            20                  25                  30

Arg Ala Asp Arg Leu Glu Met Ile Ile Asn Asp Asn Val Ser Thr Ile
        35                  40                  45

Leu Ala Ser Ile
    50

<210> SEQ ID NO 3
<211> LENGTH: 156
<212> TYPE: DNA
<213> ORGANISM: Artificial Sequence
<220> FEATURE:
<223> OTHER INFORMATION: Nucleotide sequence encoding the RHCC
      polypetide chain fragment of tetrabrachion

<400> SEQUENCE: 3
cgatccatca tcaacgaaac cgctgacgac atcgtttacc gtcgtaccgt tatcatcgac      60
gaccgttacg aatctctgaa aaacctgatc accctgctgg ctgaccgtct ggaaatgatc    120
atcaacgaca ccgtttctac catcctggct tctatc                              156
```